United States Patent [19]

Durden, Jr. et al.

[11] 4,104,043

[45] Aug. 1, 1978

[54] ESTERS OF 3-HYDROXYINDONE COMPOUNDS AS HERBICIDES AND MITICIDES

[75] Inventors: John A. Durden, Jr., South Charleston; Anthony A. Sousa, St. Albans, both of W. Va.; John F. Stephen, New City, N.Y.

[73] Assignee: Union Carbide Corporation, New York, N.Y.

[21] Appl. No.: 314,370

[22] Filed: Dec. 12, 1972

[51] Int. Cl.² ............................................. A01N 9/24
[52] U.S. Cl. ........................................ 71/107; 424/263; 424/275; 424/314; 424/301; 424/305; 260/251 R; 424/308; 424/309; 260/293.62; 424/311; 424/312; 260/295 F; 560/28; 560/55; 260/295.5 B; 560/61; 560/64; 260/332.2 C; 560/100; 560/107; 260/347.5; 560/112; 560/121; 544/106; 560/124; 560/128; 260/463; 560/129; 560/152; 260/455 B; 560/155; 560/157; 260/465 D; 560/163; 560/173; 260/465.4; 560/188; 560/221; 260/410.5; 560/228; 560/255; 560/1; 560/8; 560/9; 560/17; 560/19; 560/20; 71/88; 71/90; 71/92; 71/94; 71/95; 71/98; 71/100; 71/105; 71/106; 71/108; 71/111; 424/248.53; 424/251

[58] Field of Search ............... 424/311, 331, 308, 309, 424/312, 314; 71/106, 107; 260/488 B, 488 DC, 410.5, 455 B, 463; 560/8, 19, 28, 1, 55, 64, 107, 121, 124, 129, 155, 157, 163, 221, 228, 255

[56] References Cited

U.S. PATENT DOCUMENTS

| | | |
|---|---|---|
| 2,802,875 | 8/1957 | Kundiger et al. ................ 424/331 |
| 3,622,632 | 11/1971 | Holland et al. ................... 424/321 |
| 3,681,436 | 8/1972 | Lynch et al. ..................... 424/311 |

*Primary Examiner*—V. D. Turner
*Attorney, Agent, or Firm*—Richard C. Stewart

[57] ABSTRACT

A new series of substituted esters of 3-hydroxyindone compounds have been found to have exceptional miticidal and herbicidal activity.

34 Claims, No Drawings

ESTERS OF 3-HYDROXYINDONE COMPOUNDS AS HERBICIDES AND MITICIDES

The novel compounds of this invention are 3-hydroxyindone compounds corresponding to the following general formula:

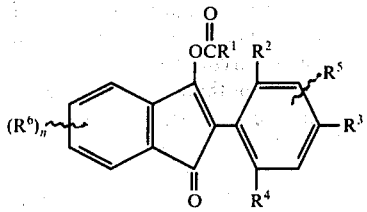

wherein:
$R^1$ is hydrogen, halogen or an organic radical;
$R^2$ is hydrogen, methyl, ethyl, methoxy, ethoxy, fluorine, chlorine, bromine, trichloromethyl or trifluoromethyl or mixed chlorofluoromethyl;
$R^3$ is hydrogen, lower alkyl, lower alkoxy, fluorine, chlorine, bromine, nitro, acylamido, trichloromethyl or trifluoromethyl;
$R^4$ is methyl, ethyl, methoxy, ethoxy, fluorine chlorine or bromine;
$R^5$ is hydrogen, lower alkyl, lower haloalkyl, lower alkoxy, acylamido, fluorine, chlorine or bromine;
$R^6$ is hydrogen, lower alkyl, lower alkoxy, fluorine, chlorine, bromine, trifluoromethyl, trichloromethyl, mixed chlorofluoromethyl or acylamido;
$n$ is a small whole number from 1 to 4; and
$R^2$ and $R^5$ or $R^3$ and $R^5$ may be taken together to form —CH=CH—CH=CH—, with the proviso that when $R^4$ is ethyl, methoxy or ethoxy, $R^2$, $R^3$ and $R^5$ may not all be hydrogen.

Compositions falling within the above generic formula exhibit biological activity as pre-emergent herbicides to a greater or lesser extent. Some exhibit very powerful pre-emergent herbicidal activity in extremely small dosages while others require larger dosages to be effective.

Miticidal activity against both the adult mite and mite ova is limited to a somewhat smaller class of compositions. In general, the compositions exhibiting this type of biological activity are those having the structural formula given above wherein:
$R^1$ is chlorine, bromine, fluorine or an organic radical, which does not interfere with hydrolysis of the ester moiety to which it is attached;
$R^2$ is hydrogen, methyl, ethyl, methoxy, fluorine, chlorine or bromine;
$R^3$ is hydrogen, lower alkyl, lower alkoxy, fluorine, chlorine or bromine;
$R^4$ is methyl, ethyl, methoxy, fluorine, chlorine or bromine;
$R^5$ is hydrogen, lower alkyl, lower alkoxy, fluorine, chlorine or bromine;
$R^6$ is hydrogen, lower alkyl, lower alkoxy, fluorine, chlorine or bromine; and
$n$ is a small whole number from 1 to 4, with the proviso that when $R^4$ is ethyl or methoxy, $R^2$, $R^3$ and $R^5$ may not all be hydrogen.

In general, these compositions also exhibit the highest degree of herbicidal activity.

Activity is greatest in compounds having an alkyl or a halo substituent in an ortho position on the 2-phenyl moiety, especially when the alkyl group is relatively small such as methyl or ethyl and preferably methyl. This is also true of alkoxy substituents and thus methoxy substituents are preferred.

The most active miticidal compositions have at least one and preferably both ortho positions of the 2-phenyl moiety substituted with either lower alkyl or halogen. Compounds having no substituents in either ortho position appear to be completely inactive both as miticides and as herbicides (See Table V). Compounds having only a single alkoxy substituent and no other substituent on the 2-phenyl ring are inactive or nearly so.

It has also been found that miticidal compositions of the class described above, wherein $R^1$ is lower alkyl having no more than four carbon atoms have excellent fumigant properties, (See Table VII below), which are not shared by other members of the class.

In general, all of the new compositions are either totally lacking in phytotoxic effect or exhibit only minimal phytotoxic properties with respect to economically important crop species tested. (See Table IX).

As indicated above, the $R^1$ substituent of the ester moiety may be halogen or essentially any organic radical including organic radicals having substituents such as halogen, nitro, alkyl, alkoxy, alkyl, thio, keto, cyano, amido etc. Illustrative of the wide range of permissible $R^1$ functions are:

Alkyl, such as methyl, t-butyl, heptadecyl, pentadecyl, chloroethyl, cyanoethyl, nitropropyl, dibromopropyl and cyanopropyl
Alkenyl, such as vinyl, allyl and undecenyl
Alkynyl, such as ethynyl and propynyl
Cycloalkyl, such as cyclopropyl, cyclopentyl, cyclohexyl, cycloheptyl and bicyclooctyl
Cycloalkenyl, such as cyclopentenyl, cyclohexenyl and methylcyclohexenyl
Alkylthioalkyl, such as methylthiomethyl, propylthioethyl, butylthioethyl and octylthiomethyl
Alkoxyalkyl, such as isopropoxymethyl, methoxymethyl and propoxyethyl
Alkoxycarbonylalkyl, such as methoxycarbonylpropyl, cyclohexyloxycarbonylethyl and butoxycarbonylbutyl
Arylalkyl such as benzyl, chlorobenzyl, nitrobenzyl, 3-phenylpropyl, phenylethyl, and 1-naphthylmethyl
Aryloxyalkyl such as phenoxyethyl, dichlorophenoxymethyl, methoxyphenoxyethyl and naphthyloxymethyl
Arylthioalkyl such as phenylthiomethyl and naphthylthiomethyl
Aryl such as phenyl, chlorophenyl, nitrophenyl, cyanophenyl, fluorophenyl, methoxyphenyl, trimethylphenyl and chloronaphthyl
Alkoxy such as methoxy, butoxy, chloromethoxy, octyloxy, dodecyloxy and ethylhexyloxy
Alkylthio such as methylthio, isopropylthio and octylthio
Aryloxy such as phenoxy and chlorophenoxy
Arylthio such as phenylthio
Heterocyclic such as furyl, thenyl, morpholino, piperidino, pyridyl and pyrimidinyl Amino such as dimethylamino, t-butylamino, methylphenylamino, 2,4,6-trimethylphenylamino, cyclohexylmethylamino and dimethylallophanyl. By way of further illustration, the amino substituents can be radicals having the formula —NR$^7$R$^8$, wherein R$^7$ is hydrogen, alkyl, alkenyl, alkynyl, cycloalkyl or aryl and R$^8$ is alkyl, alkenyl, alkynyl, cycloalkyl or aryl or R$^7$ and R$^8$, taken together, form a lower alkylene or lower dialkylene ether linkage.

Acylamidoalkyl such as acetamidomethyl and propionamidoethyl
Carbamoylalkyl such as carbamoylmethyl and N,N-dimethylcarbamoylethyl From the test data below, it will be seen that within broad limits the character of the R$^1$ group has little or no effect upon the activity of the enol ester composition. Steric effects of very large aliphatic substituents have a minimal influence on the activity of the respective acyloxyindone as compared to the cases where R$^1$ is lower alkyl (Table IV). However, when R$^1$ is phenyl having substituents in the two ortho positions, substantial impairment of both herbicidal and miticidal activity results. This is clearly due to steric inhibition, however, this undesirable steric effect may be overcome by electronic effects since compositions having substituents in both ortho positions and in the meta position did have activity at relatively low doses. It is believed that the function of the ester grouping in the novel compositions of this invention is to facilitate movement of the composition to the proper situs within the pest. The first step in the eventual destruction of the pest is believed to involve hydrolysis of the enol ester to the parent indanedione composition and, thus, the degree to which the composition is susceptible to hydrolysis plays an important role in its overall biological activity. Compositions wherein R$^1$ is a phenyl group substituted only in both ortho positions exhibit severely reduced biological activity, presumably because they are not readily hydrolyzable. The R$^1$ group is, therefore, preferably one in which the ester moiety is relatively hydrolyzable.

In general, enol ester compositions of this invention can be prepared conveniently by the reaction of an indandione with acid anhydride or acid halide in accordance with the following general reaction scheme:

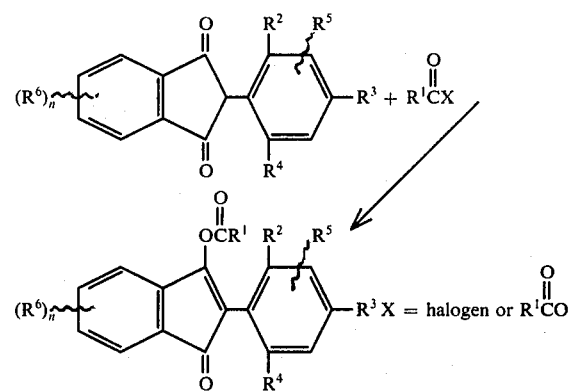

The reaction is preferably carried out in the presence of an acceptor such as N,N-dimethylaniline, pyridine, alpha-picoline, any lutidine, collodine or a tertiary aliphatic amine in a suitable solvent such as acetone, chloroform, toluene, dimethylformamide or the like. Inorganic basis such as potassium carbonate may also be employed. The reaction is not temperature sensitive and may be conducted over a broad range to yield the desired product.

The enol ester compositions in which R$^1$ is halogen can be prepared by reacting the appropriate indandione with the appropriate carbonyl halide. Enol ester compositions in which R$^1$ is amino are prepared by reacting the appropriate amine with a 3-halocarbonyloxy substituted indone.

The indandiones used as starting materials in the preparation of the indone ester compounds of this invention can be prepared by reacting an appropriately substituted benzaldehyde composition with an appropriately substituted phthalide composition as described in U.S. patent application Ser. No. 816,024 filed Apr. 14, 1969 and U.S. Pat. No. 3,622,632.

The following representative specific examples are presented to more clearly illustrate the methods used to prepare the novel compositions of this invention.

EXAMPLE I

Preparation of 3-Acetoxy-2-(2',4',6'-Trimethylphenyl)Indone

A suspension of 2.64 g (0.01 mole) of 2-(2',4',6'-trimethylphenyl)-1,3-indandione in 50 ml of acetic anhydride was treated with two drops of pyridine. After stirring for three hours the solid had dissolved and the clear solution was concentrated in vacuo at 60°. The residue was taken up in ether, washed with cool potassium bicarbonate solution and water, and the ether solution was dried over magnesium sulfate. Filtration followed by evaporation produced a solid which was recrystallized from hexane to give the desired product, M.P. 115°–116°.

EXAMPLE II

Preparation of 3-Isopropyloxycarbonyloxy-2-(2',4',6'-Trimethylphenyl)Indone

To a mixture of 9.2 g. (0.035 mole) of 2-(2',4',6'-trimethylphenyl)-1,3-indandione, 4.0 g. of pyridine and 200 ml. of hydrocarbon stabilized chloroform, was added dropwise with stirring, 4.3 g. (0.035 mole) of isopropyl chloroformate at 25°–30° C. After the addition was completed the reaction mixture was stirred at room temperature for two days, then added to 200 ml. of 10 percent hydrochloric acid. The mixture was stirred for three minutes and the chloroform layer was separated and washed two times with water, then dried with magnesium sulfate. The chloroform was removed in vacuo and the yellow oily residue was dissolved in n-hexane and treated with charcoal for 10 minutes. This mixture was filtered and the filtrate concentrated to a crystalline residue which was recrystallized from isopropanol to give 10 g. of a yellow solid. M.P. 95°–96° C.

EXAMPLE III

Preparation of 2-(2',4',6'-Trimethylphenyl)-3-Pivaloyloxyindone

To a stirred slurry of 2128 g. (8.6 moles) of 2-(2',4',6'-Trimethylphenyl)-1,3-indandione in 8000 ml of isopropyl ether was added 1420 g. (18 moles) of dry pyridine followed by 1089 g. (9 moles) of pivaloyl chloride. When addition of the pivaloyl chloride was complete the reaction mixture was heated at reflux for 0.5 hour and, after cooling, the resulting solution was extracted with 2 × 2000 ml of water, 1 × 1000 ml of 50-volume percent hydrochloric acid, and again with water. Concentration of the isopropyl ether solution in vacuo produced, in three successive fractions, 2792 g. (93.2 percent) of product, M.P. 105°–106°.

EXAMPLE IV

Preparation of 3-(2-Ethylhexanoyloxy)-2-(2',4',6'-Trimethylphenyl)Indone

A suspension solution of 520 grams (2.0 moles) of 2-(2',4',6'-trimethylphenyl)-1,3-indandione in 2 liters of toluene containing 212 grams (2.1 moles) of triethylamine was stirred at room temperature for one hour and then 325 grams (2.0 moles) of 2-ethylhexanoyl chloride was added with stirring at 30° to 40° (with some cooling) over a period of 20 minutes. The resulting deep red mixture was stirred at 30° to 35° for three hours and then at room temperature overnight.

The by-product triethylamine hydrochloride was collected and washed with toluene. The combined filtrates were washed with 10 percent hydrochloric acid and then with water until neutral. After drying over mangesium sulfate, the toluene solution was concentrated to produce a solid residue which was recrystallized from hexane with charcoal treatment. There was obtained 580 grams (75.2 percent) of product, M.P. 65°–67° C.

EXAMPLE V

Preparation of 3-Stearoyloxy-2-(2',4',6'-Trimethylphenyl)Indone

To a solution of 66 g. (0.25 mole) of 2-(2',4',6'-trimethylphenyl)-1,3-indandione, 22 g. of pyridine and 600 ml. of hydrocarbon stabilized chloroform was added dropwise with stirring at 25°–30° C., 76 g. (0.25 mole) of stearoyl chloride. After the addition was completed, the reaction mixture was stirred for 20 hours at 28° C. The mixture was then added to 500 ml. of 10 percent hydrochloric acid and stirred for 5 minutes. The chloroform layer was separated and washed two times with water then with 300 ml. of 5 percent potassium bicarbonate and finally washed until neutral with water. The organic layer was dried with magnesium sulfate, and then the chloroform was removed in vacuo. The yellow oily residue was dissolved in n-hexane and allowed to stand at 28° C. for 3 hours while a small amount of solid separated (starting 2-(2',4',6'-trimethylphenyl)-1,3-indandione). This was removed and the filtrate concentrated to a very viscous oily residue which was treated with n-hexane and cooled to −10° C. The resulting crystalline solid was filtered and washed with cold n-hexane to give 108 g., M.P. 31°–32° C.

EXAMPLE VI

Preparation of 3-(2-Ethylhexyloxycarbonyloxy)-2-(2',4',6'-Trimethylphenyl)Indone To a solution of 9.2 g. (0.035 mole) of 2-(2',4',6'-trimethylphenyl)-1,3-indandione, 4.0 g. of pyridine, and 200 ml. of hydrocarbon stabilized chloroform was added dropwise with stirring 6.8 g. (0.035 mole) of 2-ethylhexyl chloroformate at 25°–30° C. After the addition was completed, the reaction mixture was stirred at 25°–30° C. for two days, then added to 200 ml. of 10 percent hydrochloric acid. The chloroform layer was separated and washed two times with water, then dried with magnesium sulfate. The chloroform was stripped from the product under reduced pressure. The yellow oily residue was dissolved in 200 ml. of n-hexane and allowed to stand at 25° C. for three hours while a small amount of 2-(2',4',6'-trimethylphenyl)-1,3-indandione separated. This solid was removed and the filtrate was treated with charcoal. The charcoal was removed by filtration and the filtrate was concentrated under reduced pressure (1.0 mm at 28°–30° C.). The product was a yellow oily residue (10 g.).

EXAMPLE VII

Preparation of 3-(4-Chlorobutanoyloxy)-2-(2',4',6'-Trimethylphenyl)Indone

4-Chlorobutyrylchloride 4.9 g. (0.035 mole) was added dropwise with stirring at 25°–32° C. to a solution of 9.2 g. (0.035 mole) of 2-(2',4',6'-trimethylphenyl)-1,3-indandione, 4.0 g. of pyridine and 200 ml. of hydrocarbon stabilized chloroform. After the addition was completed, the mixture was stirred at 28° C. for 2 days, then added to 200 ml. of 10 percent hydrochloric acid, and stirred for 2 minutes. The chloroform layer was separated and washed two times with water, then dried with magnesium sulfate. The chloroform was removed from the product under reduced pressure. The resulting solid residue was recrystallized from isopropanol to give 11 g. of a yellow solid. M.P. 98°–100° C.

EXAMPLE VIII

Preparation of 3-Benzoyloxy-2-(2',6'-Dichlorophenyl)Indone

A stirred solution of 2-(2',6'-dichlorophenyl)-1,3-indandione (3.84 g., 0.0132 mole) in 13 ml. of pyridine was treated with benzoyl chloride (1.4 g., 0.01 mole) at room temperature. After the addition was completed the mixture was stirred at room temperature for 16 hours and then poured into dilute hydrochloric acid. The precipitated solid was collected by filtration and then dissolved in ether. The ether solution was washed with dilute hydrochloric acid and then with water (3 × 50 ml.). The dried (MgSO$_4$) ether solution was evaporated under reduced pressure to furnish a solid residue which was recrystallized from ethanol to give 1.7 g. (33%) of 3-benzoyloxy-2-(2',6'-dichlorophenyl)indone, M.P. 154°–156° C.

EXAMPLE IX

Preparation of 3-(2-Methylbenzoyloxy)-2-(2',4',6'-Trimethylphenyl)Indone

A mixture of 2-(2',4',6'-trimethylphenyl)-1,3-indandione (7.92 g. 0.03 mole) and o-toluoyl chloride (5.1 g., 0.033 mole) in 30 ml. of pyridine was stirred at room temperature for 20 hours. The mixture was poured into 300 ml. of 10% hydrochloric acid. The oil which separated was extracted with ether and the ether extract was washed with water (2 × 75 ml.). The dried MgSO$_4$) ether solution was evaporated under reduced pressure and the residue thus obtained was recrystallized from ethanol to afford 7.6 g. (66%) of product, M.P. 116°–118° C.

EXAMPLE X

Preparation of 3-(3-Nitrobenzoyloxy-2-(2',6'-Dichlorophenyl)Indone

A mixture of 2-(2',6'-dichlorophenyl)-1,3-indandione (8.73 g., 0.03 mole) and m-nitrobenzoyl chloride (6.12 g., 0.033 mole) in 30 ml. of pyridine was stirred at room temperature for 20 hours. The mixture was added to 300 ml. of 10% hydrochloric acid, and the precipitated solid was collected by filtration. Recrystallization from ethanol afforded 8.0 g. (61%) of the tile compound, m.p. 182°–185° C.

EXAMPLE XI

Preparation of 2-(2',4',6'-Trimethylphenyl)-3-Chlorocarbonyloxyindone

To a solution of 25 grams (0.25 mole) of phosgene in 200 ml of benzene was added with stirring at 25° C a solution of 26 grams (0.1 mole) of 2-(2',4',6'-trimethylphenyl)-1,3-indandione and 14 grams (0.11 mole) of N,N-dimethylaniline in 200 ml of benzene over a 10 minute period. The resulting mixture was stirred at 35° for 8 hours and then filtered. The resulting filtrate was concentrated in vacuo and the yellow residual oil was taken up in hexane and left overnight. After filtering, the hexane solution was concentrated in vacuo to a residue which crystallized. After washing with cold hexane and drying this crystalline residue amounted to 25 grams (77 percent yield), M.P. 95°–97°. The infrared spectrum (Nujol) was consistent with the desired compound showing bonds at ($\mu$): 5.6 (ClC(O)O—); 5.78 (keto C=O), 6.03 (C=C); 6.19 and 6.21 (arom. C=C), 8.9 (C—O— of ester); 11.25 (isolated arom. H); 13.1 (4 adj. arom. H). The nmr spectrum (CDCl$_3$) showed the following bands ($\delta$, ppm): 2.18, 2.22 (two singlets, ratio 2:1, 3 arom. $\underline{CH_3}$, 9H); 6.92 (singlet, isol. arom. H; 2H); 7.02–7.62 (complex mult., arom. H, 4H).

EXAMPLE XII

Preparation of 2-(2',4',6'-Trimethylphenyl)-3-n-(t-Butyl)Carbamoyloxyindone

To a solution of 12 grams (0.038 mole) of 3-chlorocarbonyloxy)-2-(2',4',6'-trimethylphenyl) indone in 150 ml of toluene was added dropwise with stirring at ambient temperature, 5.6 grams (0.076 mole) of t-butylamine. After stirring for 1 hour at room temperature the reaction mixture was filtered and the filtrate concentrated in vacuo to produce a yellow oily residue. This was dissolved in ethyl ether, and, after a thorough water wash, the ether solution was dried over magnesium sulfate, treated with charcoal and finally filtered. This filtrate was concentrated in vacuo to give a solid residue which was recrystallized from isopropyl alcohol to provide 8 grams (63.8 percent) of product, M.P. 145°–147°; ir., Nujol ($\mu$): 2.98 (NH); 5.61 (enol CO); 5.9 (keto CO), 6.02 (conj, C=C); 6.22 (arom. C=C); 7.21, 7.23 (t—C(CH$_3$)$_3$); 8.9 (C—O—) nmr, CDCl$_3$ ($\delta$, ppm): 1.19 (singlet, C(CH$_3$)$_3$, 9H); 2.18, 2.24 (pair of singlets, ratio 2:1, arom. $\underline{CH_3}$, 9H); 5.4 (broad singlet, NH, 1H); 6.89 (singlet, isol. arom. H. 2H); 7.0–7.6 (complex mult., 4 arom. H, 4H).

EXAMPLE XIII

Preparation of 2-(2',4',6'-Trimethylphenyl)-3-(4-Morpholino)Carbonyloxyindone

Using the same procedure used in Example XII above, but substituting 6.6 grams (0.076 mole) of morpholine for t-butylamine, there was obtained as a residual yellow solid, 11 grams (77 percent), M. P. 43°–47°. The infrared spectrum was consistent with proposed structure.

EXAMPLE XIV

Preparation of 2-(2',4',6'-Trimethylphenyl)-3-(2,4-Dimethylallophanoyloxy)Indone To a mixture of 9.2 grams (0.035 mole) of 2-(2',4',6'-trimethylphenyl)-1,3-indandione and 200 ml of toluene was added 4 grams (excess) of triethylamine and the resulting mixture was stirred at ambient temperature for 30 minutes. To this stirred mixture was then added 5.3 grams (0.035 mole) 2,4-dimethylallophanoyl chloride and the resulting solution was heated at 45° for four hours after which the mixture was cooled and filtered. The filtrate was washed 4 times with water, dried over magnesium sulfate, and finally concentrated in vacuo to a residue which was dissolved in hexane and treated with charcoal. Removal of the hexane in vacuo produced a residual oil which was taken as product, 10 grams (75.5 percent yield); ir. (capillary) ($\mu$): 2.95 (NH); 5.75 (enol carbamate C=O); 5.80 (ketone C=O); 5.83 (shoulder —NHC(O)N); 6.09 (enol C=C); 6.25 (arom. C=C), 8.9/7.8 C—O—).

EXAMPLE XV

Preparation of Bis[2-(2',4',6'-Trimethylphenyl)Indon-3-yl]Carbonate

To a solution of 20 grams of phosgene in 200 ml of toluene was added dropwise with stirring at ambient temperature a solution of 26 grams (0.1 mole) of 2-(2',4',6'-trimethylphenyl)-1,3-indandione and 12 grams (0.12 mole) of triethylamine in 200 ml of toluene. The mixture was stirred at room temperature for 2 hours and was then concentrated to about one-half volume. The remaining solution was washed twice with cold water and then dried over magnesium sulfate. Filtration and subsequent concentration of the filtrate in vacuo produced a yellow solid, 20 grams (72 percent yield), M.P. 221°–223°. The infrared and nmr spectra are consistent with the proposed structure.

EXAMPLE XVI

Preparation of 3-Acetoxy-2(2',6'-Dichlorophenyl)-4 (and 7- )-Methylindone

To a solution of 3.05 gram (0.01 mole) of 2-(2',6'-dichlorophenyl)-4-methyl-1,3-indandione in 50 ml of acetic anhydride was added 3 drops of pyridine and the resulting yellowish solution was stirred at room temperature for 3 hours. The mixture was then concentrated in vacuo to a solid residue which was taken up in ether, and the resulting solution was washed with ice water and then dilute sodium bicarbonate solution and finally dried over magnesium sulfate. Filtration and subsequent concentration of the filtrate in vacuo to produce a yellow crystalline residue which was crystallized from isopropyl ether to yield 2.3 grams (66.2 percent) of product, M.P. 101°–120°. The infrared and nmr spectra were consistent with the desired structure. These, together with the elemental analysis, show the material to be a mixture of the isomers indicated in the title of this Example.

The following specific compositions in addition to those described in the Examples and in Tables I–IV below are illustrative of the new compositions of this invention:

3-(3-cyanopropionyloxy)-2-(2',6'-dimethylphenyl)indone
3-(acetamidoacetyloxy)-2-(2'-chloro-4',6'-dimethyl)indone
3-(2-methyl-2-nitropropionyloxy)-2-(2',4',6'-trimethylphenyl)indone
3-(diphenylacetyloxy)-2-(2',6'-dichlorophenyl)indone
3-(4-cyanobenzoyloxy)-2-(2',4',6'-trimethylphenyl)indone
3-(4-methylthiobenzoyloxy)-2-(2'-methyl-6'-ethylphenyl)indone
3-acetoxy-2-(2',4'-dimethyl-6'-ethylphenyl)indone
3-(3-methylbutyryloxy)-2-(2'-chloro-6'-ethylphenyl)indone
3-crotonoyloxy-2-(2'-bromo-6'-chlorophenyl)indone
3-(2-butynoyloxy)-2-(2'-methoxy-6'-methylphenyl)indone
3-cyclobutanoyloxy-2-(2'-bromo-6'-methylphenyl)indone
1-cyclopent-2-enoyloxy-2-(2',6'-dibromophenyl)indone
3-(4-bromobutyryloxy)-2-(2',6'-dimethyl-4'-ethylphenyl)indone
3-(2-methylthiopropionyloxy)-2-(2',6'-dichloro-4-methylphenyl)indone
3-(3-ethoxybutyryloxy)-2-(2'-chloro-4',6'-diethylphenyl)indone
3-(3-ethoxycarbonylbutyryloxy)-2-(2'-bromo-6'-fluorophenyl)indone
3-(2-phenylbutyryloxy)-2-(2',6'-dibromo-4'-methylphenyl)indone
3-(3-phenoxypropionyloxy)-2-(2',6'-dichloro-4'-fluorophenyl)indone
3-phenylthioacetoxy-2-(2'-chloro-6'-methylphenyl)indone
3-benzoyloxy-2-(2',6'-dimethyl-4'-isopropylphenyl)indone
3-(4-bromobenzoyloxy)-2-(2',4'-dichloro-6'-methoxyphenyl)indone
3-(3-isopropylbenzoyloxy)-2-(2'-methyl-6'-trifluoromethylphenyl)indone
3-(4-ethoxybenzoyloxy)-2-[2'-(t-butyl)-6'-methylphenyl]indone
3-(3,5-dinitrobenzoyloxy)-2-(2',6'-dimethoxy-4'-methylphenyl)indone
3-formyloxy-2-(2'-ethyl-6'-methylphenyl)indone
3-chlorocarbonyloxy-2-(2',6'-dimethyl-4'-chlorophenyl)indone
3-(isobutyloxycarbonyloxy)-2-(2',4'-dimethyl-6'-chlorophenyl)indone
3-(ethylthiocarbonyloxy)-2-(2'-fluoro-6'-methylphenyl)indone
3-(phenoxycarbonyloxy)-2-(2'-ethoxy-4',6'-dimethylphenyl)indone
3-(phenylthiocarbonyloxy)-(2',6'-dimethyl-4'-trifluoromethylphenyl)indone
3-(N-isopropylcarbamoyloxy)-2-(2',6'-diethylphenyl)indone
3-(N-hexyl-N-ethylcarbamoyloxy)-2-(2'-bromo-6'-ethylphenyl)indone
3-(N-allyl-N-methylcarbamoyloxy)-2-(2',6'-dimethyl-4'-isopropylphenyl)indone
3-(N,N-dicrotylcarbamoyloxy)-2-(2'-methoxy-4',6'-dimethylphenyl)indone
3-(N,N-dipropargylcarbamoyloxy)-2-(2'-methyl-4',6'-diethylphenyl)indone
3-(N-cyclopentyl-N-methylcarbamoyloxy)-2-(2',6'-dimethyl-4'-chlorophenyl)indone
3-[N-(4-methylphenyl)-N-ethylcarbamoyloxy]-2-(2',6'-dimethyl-4'-methoxyphenyl)indone
3-(heptanoyloxy)-2-(2',4',6'-trimethyl-3'-ethylphenyl)indone
3-(2-ethylpentanoyloxy)-2-(2',4'-dimethyl-6'-chloro-3'-methoxyphenyl)indone
3-(3-hexenoyloxy)-2-(2',5'-dichloro-6'-methylphenyl)indone
3-(propynoyloxy)-2-(2',3',6'-trimethylphenyl)indone
3-(cyclopropanoyloxy)-2-(2',6'-dimethyl-3'-chlorophenyl)indone
3-(2-bicyclooct-5-encarbonyloxy)-2-(2',6'-dimethyl-3'-bromophenyl)indone
3-(6-chloroheptanoyloxy)-2-(2',6'-dimethyl-3'-methoxyphenyl)indone
3-(3-propylthiopropionyloxy)-2-(2',6'-dimethyl-3'-fluorophenyl)indone
3-(3-methoxypropionyloxy)-2-(2'-methyl-3'-chloro-6'-methoxyphenyl)indone
3-[3-(butoxycarbonyl)propionyloxy]-2-(2'-methyl-6'-trifluoromethyl-3'-fluorophenyl)indone
3-[(4-chlorophenyl)acetoxy]-2-(2',6'-dichloro-3'-bromophenyl)indone
3-[2-(2-chloro-4-methylphenoxy)propionyl]-2-(2'-ethyl-6'-methyl-3'-chlorophenyl)indone
3-(4-chlorophenylthioacetoxy)-2-(2',6'-dichloro-3',4'-dimethylphenyl)indone
3-(benzoyloxy)-2-(2',6'-dimethyl-3',4'-dichlorophenyl)indone
3-(2,4,5-trichlorobenzoyloxy)-2-(2',3',4',6'-tetramethylphenyl)indone
3-(3,5-dimethylbenzoyloxy)-2-(2',6'-dichloro-3'-methylphenyl)indone
3-(3,4,5-trimethoxybenzoyloxy)-2-(2',3',4'-trimethyl-6'-methoxyphenyl)indone
3-(4-nitro-3-methylbenzoyloxy)-2-(2',4',6'-trichloro-3'-methylphenyl)indone
3-(formyloxy)-2-(2',3'-diethyl-6'-methylphenyl)indone
3-(chlorocarbonyloxy)-2-(2',4',6'-trimethyl-3'-chlorophenyl)indone
3-(chloroethoxycarbonyloxy)-2-(2',4',6'-trimethylphenyl)indone
3-(ethoxycarbonylmethylthiocarbonyloxy)-2-(2'-chloro-6'-methylphenyl)indone
3-(allylthiocarbonyloxy)-2-(2',6'-dimethylphenyl)indone
3-(2,4-dichlorophenylthiocarbonyloxy)-2-(2',4'-dimethyl-6'-ethylphenyl)indone
3-[4-(acetamido)phenoxycarbonyloxy]-2-(2',6'-dimethyl-4'-ethyl-3'-chlorophenyl)indone
3-[N,N-di(n-propyl)carbamoyloxy]-2-(2',4',6'-trimethyl-3'-bromophenyl)indone
3-propionyloxy-2-(2',4',6'-trimethylphenyl)-5-ethyl indone
3-acetoxy-2-(2',6'-dichlorophenyl)-5-t-butylindone
3-(2-ethylhexanoyloxy)-2-(2',4',6'-trimethylphenyl)-4,6-dimethylindone
3-(cyclopropanecarbonyloxy)-2-(2',6'-dichlorophenyl)-5,6-dichloroindone
3-[2-ethoxycarbonyl-2-methylpropionyloxy]-2-(2',6'-dichlorophenyl)-4-chloro-5-methylindone
3-(pivaloyloxy)-2-(2',4',6'-trimethylphenyl)-5-bromoindone
3-(2-ethylhexanoyloxy)-2-(2',4',6'-trimethylphenyl)-5,7-dimethylindone
3-(pivaloyloxy)-2-(2',4',6'-trimethylphenyl)-5-fluoroindone 3-(isobutyroxy)-2-(2',6'-dimethylphenyl)-5-methoxyindone
3-(pivaloyloxy)-2-(2'-trichloromethyl-6'-methylphenyl)indone
3-(isobutyroxy)-2-(2'-trifluoromethyl-4',6'-dichlorophenyl)indone
3-acetoxy-2-(2',6'-dimethyl-4'-nitrophenyl)indone
3-(propionyloxy)-2-(2',6'-dichloro-4'-acetamidophenyl)indone
3-(butyryloxy)-2-(2'-methyl-4'-trifluoromethylphenyl)indone
3-(pivaloyloxy)-2-(2',6'-dichloro-4'-trichlorophenyl)indone
3-(pivaloyloxy)-2-(2',6'-dichloro-4'-chlorodifluoromethylphenyl)indone
3-acetoxy-2-(2'-dichlorofluoromethyl-4',6'-dichlorophenyl)indone
3-(benzoyloxy)-2-(2',4',6'-trimethyl-3'-formamidophenyl)indone
3-acetoxy-2-(2',4'-dimethyl-5'-trifluoromethylphenyl)indone
3-(butyryloxy-2-(2',4',6'-trichloro-3'-dichlorofluoromethylphenyl)indone
3-(4-chloronaphthylcarbonyloxy)-2-(2',4',6'-trimethylphenyl)indone
3-(methoxycarbonyloxy)-2-(2'-methylphenyl)indone
3-(propoxycarbonyloxy)-2-(2',6'-diethylphenyl)indone
3-(isopropylthiocarbonyloxy)-2-(2'-chloro-6'-ethylphenyl)indone
3-(methoxyethylthiocarbonyloxy)-2-(2',4',6'-trimethylphenyl)indone 3-(2,4-dimethylphenoxycarbonyloxy)-2-(2',6'-dimethylphenyl)indone
3-(pyrimidin-5-yl carbonyloxy)-2-(2'-bromophenyl)indone
3-(3-propionamidoethylcarbonyloxy)-2-(2',6'-dichlorophenyl)indone
3-(carbamoylmethylcarbonyloxy)-2-(2',4',6'-trimethylphenyl)indone
3-(N,N-dimethylcarbamoylethylcarbonyloxy)-2-(2'-chloro-6'-bromophenyl)indone
3-(2-nitroethylcarbonyloxy)-2-(2'-ethyl-6'-methylphenyl)indone
3-(3-cyanobutyryloxy)-2-(2'-bromo-6'-fluorophenyl)indone
3-(2,3-dibromopropionyloxy)-2-(2',4',6'-trimethylphenyl)indone
3-(acryloyloxy)-2-(2',6'-dimethylphenyl)indone
3-(propioloyloxy)-2-(2'-bromo-6'-methylphenyl)indone
3-(2-norborn-5-enecarbonyloxy)-2-(2',6'-dichlorophenyl)indone
3-(cycloheptanecarbonyloxy)-2-(2'-bromo-6'-methylphenyl)indone
3-(octylthioacetoxy)-2-(2',6'-dibromophenyl)indone
3-(3-isopropoxypropionyloxy)-2-(2',4',6'-triethylphenyl)indone
3-(3-cyclohexyloxycarbonylpropionyloxy)-2-(2'-bromo-6'-ethylphenyl)indone
3-(3-nitrophenylacetyloxy)-2-(2',6'-dimethylphenyl)indone
3-(1-naphthaleneacetyloxy)-2-(2',4',6'-trimethylphenyl)indone
3-(2-naphthyloxyacetoxy)-2-(2'-bromophenyl)indone
3-[3-(1-naphthylthio)propionyloxy]-2-(2',4',6'-trimethylphenyl)indone Selected enol ester compounds, representative of those useful in accordance with this invention were tested with respect to their miticidal and herbicidal activity.

Suspensions of the test compounds were prepared by dissolving one gram of compound in 50 milliliters of acetone in which had been dissolved 0.1 gram (10 percent of the weight of compound) of an alkylphenoxyethanol surfactant, as an emulsifying or dispersing agent. The resulting solution was mixed into 160 milliliters of water to give roughly 200 milliliters of a suspension containing the compound in finely divided form. The thus-prepared stock suspension contained 0.5 percent by weight of compound. The test concentrations employed in the tests described hereinbelow were obtained by diluting the stock suspension with water. The test procedures were as follows:

Mite Foliage Spray Test

Adults and nymphal stages of the two-spotted mite (tetranychus urticae (Koch)), reared on Tendergreen bean plants at 80°±5° F. and 50±5 percent relative humidity, were the test organisms. Infested leaves from a stock culture were placed on the primary leaves of two bean plants 6 to 8 inches in height, growing in a 2½ inch clay pot. 150-200 Mites, a sufficient number for testing, transferred from the excised leaves to the fresh plants in a period of twenty-four hours. Following the 24 hour transfer period, the excised leaves were removed from the infested plants. The test compounds were formulated by diluting the stock suspension with water to provide suspensions containing the desired amount of test compound per million parts of final formulation. The potted plants (one pot per compound) were placed on a revolving turntable and sprayed with 100-110 milliliters of test compound formulation by use of a DeVilbis spray gun set at 40 psi. air pressure. This application, which lasted 30 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80°±5° F. and 50±5 percent relative humidity for 4 days, after which, a mortality count of motile forms was made. Microscopic examination for motile forms was made on the leaves of the test plants. Any individual which was capable of locomotion upon prodding was considered living.

Mite Ovicide Test

The test organism was the egg of the two-spotted mite (*Tetranychus urticae* (Koch)), as obtained from adults reared on Tendergreen bean plants under controlled conditions of 80°±5° F. and 50±5 percent relative humidity. Heavily infested leaves from a stock culture were placed on the primary leaves of two bean plants 6 to 8 inches in height, growing in a two-and-a-half inch clay pot. Females were allowed to oviposit for a period of 48 hours and then the leaves of the infested plants were dipped in a solution containing 800 parts of tetraethyl pyrophosphate per million parts of water in order to destroy the reproductory forms and thus prevent further egg laying. This solution of tetraethyl pyrophosphate does not affect the viability of the eggs. The plants were allowed to dry thoroughly. The test compounds were formulated by diluting the stock suspension with water to give a suspension containing varying amounts of test compound per million parts of final formulation. The potted plants (one pot per compound) were placed on a revolving turntable and sprayed with 100–110 milliliters of test compound formulation by use of a DeVilbis spray gun set at 40 psig. air pressure. This application, which lasted 30 seconds, was sufficient to wet the plants to run-off. As a control, 100–110 milliliters of a water solution containing acetone and emulsifier in the same concentrations as the test compound formulation, but containing no test compound, were also sprayed on plants infested with eggs. The sprayed plants were held at 80°±5° F. and 50±5 percent relative humidity for 4 days, after which a microscopic examination was made of unhatched (dead) and hatched (living) eggs.

Compositions were rated on the basis of percent kill with a rating of 1 indicating no injury; 3 signifying an approximately 50% mortality and 5 indicating 100% mortality at the indicated dosage.

Preliminary Herbicide Seed Germination Test

The following seeds were used in this test:
Perennial rye grass — *Solium perenne*
Crabgrass — *Digitaria sanguinalis*
Red root pigweed — *Amaranthus retroflexus*
Mustard — *Brassica pincea* var. foliosa (Florida broadleaf)

Two seed-soil mixtures were prepared as follows:
Mixture I
  196 cc. Rye grass seed
  75 cc. Mustard seed
  18,000 cc. Sifted, fairly dry soil
Mixture II
  99 cc. Crabgrass seed
  33 cc. Amaranthus
  18,000 cc. Sifted, fairly dry soil Each of above mixtures is rolled separately in 5 gallon containers for approximately one-half hour on ball mill to insure uniform mixing of seeds and soil. For each compound four 3-inch pots are filled with soil to within 1¼ inches of top of pots. To 2 of these pots are added 70 cc. of Mixture I. To the remaining 2 pots are added 70 cc. of Mixture II. The seed-soil mixture is tamped firmly, and the pots are removed to the greenhouse and watered lightly. About 2 hours after planting, 25 milliliters of the test formulation were added to each of 2 pots for each soil-seed mixture; i.e., one replicate of each seed mixture per concentration. An equal volume of a water solution containing acetone and an emulsifier in the same concentration as the herbicidal mixture but without the candidate herbicide is also added to each of the soil-seed mixtures. These pots are used as check or control units. The test compounds are formulated by standard procedure of solution in acetone, addition of an emulsifier, and dilution with water. Tests were conducted on all compositions at low concentration (100 ppm.). Certain compositions were also tested at high concentration (1000 ppm). The pots were held in the greenhouse and watered lightly until results were taken. Ten to 12 days after application of chemical, injury is noted for each species by comparing treated vs. untreated pots. Ratings are made at both the high and the low concentrations (1000 ppm and 100 ppm) according to the following designations:

5 = no seedlings emerged
4 = few seedlings emerged and/or very severe stunting
3 = moderate reduction in stand and/or moderate stunting
2 = very slight reduction in stand and/or slight stunting
1 = no injury; seedlings appear no different with respect to stand or growth than untreated controls Accordingly, the maximum rating for one test seed species tested at both high and low concentration is 10 and the maximum possible total preemergence rating is 40 (10 for each of the four test seed species). For those tested only at low concentration, the maximum rating is 20. In the Tables below, herbicidal test results are shown as a fraction in which the numerator is the actual rating achieved. In some tests the crabgrass experiment was omitted. In these tests the maximum total rating for species tested at both high and low concentrations is 30 and 15 for species tested only at low concentrations.

In Table I below all of the compounds tested have a methyl substituent in each of the 2,4 and 6 positions on the 2-phenyl moiety and a substituted phenyl group directly bonded to the carbonyl of the ester group. This Table illustrates the effect of varying the number and position of substituents on an aryl group attached to the ester moiety.

Table II is similar to Table I but differs in that the 2-phenyl moiety carries a chloro substituent at each of the 2 and 6 positions.

In Table III all of the compounds tested include an alkyl group attached to the carbonyl of the ester while the 2-phenyl moiety is variously substituted, but always includes a substituent in one of the ortho positions of the 2 phenyl moiety.

In Table IV below the 2-phenyl moiety of all of the compounds tested carries methyl substituents at the 2, 4 and 6 positions and differ from each other only in the character of the ester moiety. The examples illustrate the nature and extent of the influence of the ester function on the biological properties of the enol ester compounds. It is to be noted that even those few compounds exhibiting little or no activity in these particular tests will be somewhat effective at higher dosage levels.

TABLE I

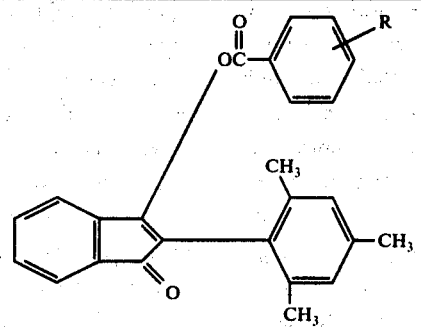

| Name | R | °C M.P. | Herbicide | Primary Mite Data Adult | Ova |
|---|---|---|---|---|---|
| 3-Benzoyloxy-2-(2',4',6'-trimethylphenyl)indone | H | 147–150 | 31/40 | 5 | 5 |
| 3-(2-Chlorobenzoyloxy)-2-(2',4',6'-trimethylphenyl)indone | 2-Cl | 108–110 | 32/40 | 5 | 5 |
| 3-(3-Chlorobenzoyloxy)-2-(2',4',6'-trimethylphenyl)indone | 3-Cl | 140–142 | 29/40 | 5 | 5 |
| 3-(4-Chlorobenzoyloxy)-2-(2',4',6'-trimethylphenyl)indone | 4-Cl | 93–95 | 24/30 | 5 | 5 |
| 3-(2-Methylbenzoyloxy)-2-(2',4',6'-trimethylphenyl)indone | 2-CH₃ | 116–118 | 19/30 | 5 | 5 |
| 3-(3-Methylbenzoyloxy)-2-(2',4',6'-trimethylphenyl)indone | 3-CH₃ | 115–117 | 26/40 | 5 | 5 |
| 3-(4-Methylbenzoyloxy)-2-(2',4',6'-trimethylphenyl)indone | 4-CH₃ | 113–116 | 22/30 | 5 | 5 |
| 3-(3-Methoxybenzoyloxy)-2-(2',4',6'-trimethylphenyl)indone | 3-OCH₃ | 112–115 | 25/30 | 5 | 5 |
| 3-(4-Methoxybenzoyloxy)-2-(2',4',6'-trimethylphenyl)indone | 4-OCH₃ | 117–120 | 21/30 | 3 | 5 |
| 3-(3-Nitrobenzoyloxy)-2-(2',4',6'-trimethylphenyl)indone | 3-NO₂ | 123–126 | 28/30 | 5 | 5 |
| 3-(4-Nitrobenzoyloxy)-2-(2',4',6'-trimethylphenyl)indone | 4-NO₂ | 165–167 | 26/30 | 5 | 5 |
| 3-(2,4-Dichlorobenzoyloxy)-2-(2',4',6'-trimethylphenyl)indone | 2,4-Cl₂ | 126–128 | 32/40 | 5 | 5 |
| 3-(3,4-Dichlorobenzoyloxy)-2-(2',4',6'-trimethylphenyl)indone | 3,4-Cl₂ | 157–159 | 32/40 | 5 | 5 |
| 3-(3,5-Dichlorobenzoyloxy)-2-(2',4',6'-trimethylphenyl)indone | 3,5-Cl₂ | 165–168 | 23/30 | 5 | 5 |
| 3-(2,6-Dichlorobenzoyloxy)-2-(2',4',6'-trimethylphenyl)indone | 2,6-Cl₂ | 168–172 | 8/40 | 1 | 1 |
| 3-(2,3,6-Trichlorobenzoyloxy)-2-(2',4',6'-trimethylphenyl)indone | 2,3,6-Cl₃ | 163–165 | 21/40 | 1 | 3 |
| 3-(2,6-Dimethoxybenzoyloxy)-2-(2',4',6'-trimethylphenyl)indone | 2,6-(CH₃O)₂ | 141–143 | 4/20 | 1 | 1 |
| 3-(2,4-Dimethylbenzoyloxy)-2-(2',4',6'-trimethylphenyl)indone | 2,4-(CH₃)₂ | 118–120 | 11/15 | 1 | 5 |
| 3-(2,4,6-Trimethylbenzoyloxy)-2-(2',4',6'-trimethylphenyl)indone | 2,4,6-(CH₃)₃ | 154–155 | 10/15 | 1 | 1 |
| 3-(2,6-Dimethylbenzoyloxy)-2-(2',4',6'-trimethylphenyl)indone | 2,6-(CH₃)₂ | 123–125 | 4/20 | 1 | 1 |

TABLE II

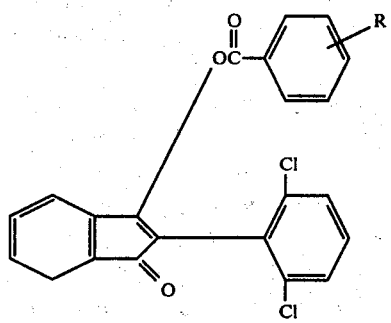

| Name | R | M.P. | Herbicide | Mite Adult | Ova |
|---|---|---|---|---|---|
| 3-(Benzoyloxy)-2-(2',6'-dichlorophenyl)indone | H | 154–156 | 32/40 | 5 | 5 |
| 3-(2-Chlorobenzyloyloxy)-2-(2',6'-dichlorophenyl)indone | 2-Cl | 106–108 | 30/40 | 5 | 5 |
| 3-(3-Chlorobenzoyloxy)-2-(2',6'-dichlorophenyl)indone | 3-Cl | 124–126 | 32/40 | 5 | 5 |
| 3-(4-Chlorobenzoyloxy)-2-(2',6'-dichlorophenyl)indone | 4-Cl | 113–116 | 23/30 | 5 | 5 |
| 3-(2-Methylbenzoyloxy)-2-(2',6'-dichlorophenyl)indone | 2-CH₃ | Residue* Product | 31/40 | 5 | 5 |
| 3-(3-Methylbenzoyloxy)-2-(2',6'-dichlorophenyl)indone | 3-CH₃ | 138–141 | 29/40 | 5 | 5 |
| 3-(4-Methylbenzoyloxy)-2-(2',6'-dichlorophenyl)indone | 4-CH₃ | 136–140 | 22/30 | 5 | 5 |
| 3-(3-Methoxybenzoyloxy)-2-(2',6'-dichlorophenyl)indone | 3-OCH₃ | 143–145 | 23/30 | 5 | 5 |
| 3-(4-Methoxybenzoyloxy)-2-(2',6'-dichlorophenyl)indone | 4-OCH₃ | 149–152 | 22/30 | 5 | 5 |
| 3-(3-Nitrobenzoyloxy)-2-(2',6'-dichlorophenyl)indone | 3-NO₂ | 182–195 | 26/30 | 5 | 5 |
| 3-(4-Nitrobenzoyloxy)-2-(2',6'-dichlorophenyl)indone | 4-NO₂ | 164–167 | 25/30 | 5 | 5 |
| 3-(2,4-Dichlorobenzoyloxy)-2-(2',6'-dichlorophenyl)indone | 2,4-Cl₂ | 138–140 | 28/40 | 5 | 5 |
| 3-(3,4-Dichlorobenzoyloxy)-2-(2',6'-dichlorophenyl)indone | 3,4-Cl₂ | 130–132 | 29/40 | 5 | 5 |
| 3-(3,5-Dichlorobenzoyloxy)-2-(2',6'-dichlorophenyl)indone | 3,5-Cl₂ | 125–130 | 24/30 | 5 | 5 |
| 3-(2,6-Dichlorobenzoyloxy)-2-(2',6'-dichlorophenyl)indone | 2,6-Cl₂ | 182–185 | 8/40 | 1 | 1 |
| 3-(2,3,6-Trichlorobenzoyloxy)-2-(2',6'-dichlorophenyl)indone | 2,3,6-Cl₃ | 210–214 | 20/40 | 5 | 5 |
| 3-(2,6-Dimethoxybenzoyloxy)-2-(2',6'-dichloro- | 2,6-(CH₃O)₂ | 226–228 | 12/15 | 1 | 1 |

TABLE II-continued

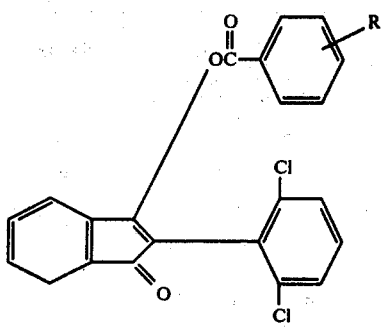

| Name | R | M.P. | Herbicide | Mite Adult | Ova |
|---|---|---|---|---|---|
| phenyl)indone | | | | | |
| 3-(2,4-Dimethylbenzoyloxy)-2-(2',6'-dichlorophenyl)indone | 2,4-(CH₃)₂ | 152–154 | 5/20 | 1 | 3 |
| 3-(2,4,6-Trimethylbenzoyloxy)-2-(2',6'-dichlorophenyl)indone | 2,4,6-(CH₃)₃ | 142–145 | 6/15 | 1 | 1 |
| 3-(2,6-Dimethylbenzoyloxy)-2-(2',6'-dichlorophenyl)indone | 2,6-(CH₃)₂ | 150–152 | 4/20 | 1 | 1** |

*Calcd for $C_{22}H_8Cl_2O_3$; C, 67.65; H, 3.45; Found C, 67.03; H, 3.72 γmax: 5.7μ (ester C=O); 6.1μ (enol double bond); 5.82μ (ketone C=O); 8.2μ (C—O stretch).
**About 20% kill at 500 ppm.

TABLE III

| Name | M.P. °C or IR | Herbicides | Mite Adult | Ova |
|---|---|---|---|---|
| 2-(2',6'-Dichlorophenyl)-3-(pivaloyloxy)indone | 133–135 | 30/40 | 5 | 5 |
| 2-(2'-Bromophenyl)-3-(pivaloyloxy)indone | 91–98 | 14/40 | 5 | 5 |
| 3-Acetoxy-2-(2'-bromophenyl)indone | 93–97 | 19/40 | 5 | 5 |
| 3-(2-Ethylhexanoyloxy)-2-(2'-fluorophenyl)indone | γmax (μ): 5.61 (ester C=O); 5.8 (ketone C=O); 6.1 (enol C=C) | 4/20 | 3 | 5 |
| 2-(2'-Chlorophenyl)-3-(pivaloyloxy)indone | 80–82 | 18/40 | 5 | 5 |
| 2-(2'-Chlorophenyl)-3-(2-methylpentanoyloxy)indone | γmax (μ): 5.62 (ester C=O), 5.8 (ketone C=O); 6.1 (enol C=C) | 4/20 | 5 | 5 |
| 2-(2'-Chlorophenyl)-3-(stearoyloxy)indone | 50–53 | 4/20 | 1 | 5 |
| 2-(2'-Chloro-6'-methylphenyl)-3-(pivaloyloxy)indone | 93–96 | 33/40 | 5 | 5 |
| 2-(2'-Methylphenyl)-3-(pivaloyloxy)indone | 62 | 20/40 | 5 | 5 |
| 3-(2-Ethylhexanoyloxy)-2-(2'-methylphenyl)indone | γmax (μ): 5.65 (enol ester); 5.81 (ketone C=O); 6.11 (enol C=C) | 4/20 | 3 | 5 |
| 2-(2'-Methylphenyl)-3-(palmitoyloxy)indone | 34–36 | 4/20 | 3 | 5 |
| 2-(2'-Methylphenyl)-3-(neodecanoyloxy)indone (mixture of isomers) | γmax (μ): 5.62 (ester C=O); 5.79 (ketone C=O); 6.1 (enol C=C) | 4/20 | 1 | 1 |
| 2-(2',4'-Dimethylphenyl)-3-(stearoyloxy)indone | γmax (μ): 5.6 (ester C=O); 5.79 (ketone C=O); 6.1 (enol C=C) | 14/20 | 3 | 5 |
| 2-(2',4'-Dimethylphenyl)-3-(lauroyloxy)indone | γmax (μ): 5.6 (ester C=O); 5.79 (ketone C=O), 6.1 (enol C=C) | 14/20 | 5 | 5 |
| 2-(2',4'-Dimethylphenyl)-3-(2-methylpentanoyloxy)indone | γmax (μ): 5.62 (ester C=O); 5.79 (ketone C=O); 6.13 (enol C=C) | 14/20 | 3 | 5 |
| 2-(2',6'-Dimethylphenyl)-3-(pivaloyloxy)indone | 82–84 | 31/40 | 5 | 5 |
| 2-(2',5'-Dimethylphenyl)-3-(neodecanoyloxy)indone (mixture of isomers) | γmax (μ): 5.63 (ester C=O); 5.8 (ketone (C=O); 6.1 (enol C'C) | 4/20 | 1 | 3 |
| 2-2',5'-Dimethylphenyl)-3-(2-ethylbutanoyloxy)indone | γmax (μ): 5.65 (ester C=O); 5.8 (deonte C=O); | 4/20 6.1 (enol C=C) | 3 | 5 |
| 2-(2',5'-Dimethylphenyl)-3-(tridecanoyloxy)indone | γmax (μ): 5.6 (ester C=O); 5.8 (ketone C=O); 6.1 (enol C=C) | 4/20 | 1 | 5 |
| 2-(2'-Ethyl-6'-methylphenyl)-3-(pivaloyloxy)indone | 69–70 | 14/15 | 5 | 5 |
| 2-(2',6'-Diethylphenyl)-3-(pivaloyloxy)indone | 98–99 | 12/15 | 5 | 5 |
| 2-(2',6'-Dimethyl-4'-t-butylphenyl)-3-(pivaloyloxy)indone | 129–133 | 9/40 | 1 | 1 |
| 2-(2',6'-Dimethyl-4'-methoxyphenyl)-3-(pivaloyloxy)indone | 123–124 | 24/40 | 3 | 3 |
| 3-(Pivaloyloxy)-2-(6'-methoxy-2',3',4'-trimethylphenyl)indone | 108–110 | 16/40 | 1 | 1 |
| 3-(2-Ethylhexanoyloxy)-2-(1-Naphthyl)indone | γmax (μ): | 14/20 | 1 | 1 |

TABLE III-continued

| Name | M.P. °C or IR | Herbicides | Mite Adult | Ova |
|---|---|---|---|---|
| | 5.67 (ester C=O); 5.81 (ketone C=O); 6.15 (enol C=C) | | | |
| 3-(Acetoxy)-4(7)-methyl-2-(2',6'-dichlorophenyl)-indone | 101–120 | 37/40 | 5 | 5 |
| 2-(2',6'-Dichlorophenyl)-4(7)-methyl-3-(pivaloyloxy)-indone | 152–154 | 20/40 | 1 | 3 |
| 2-(2',6'-Dichlorophenyl)-5(6)-methyl-3-(pivaloyloxy)-indone | 158–160 | 24/40 | 5 | 5 |

TABLE IV

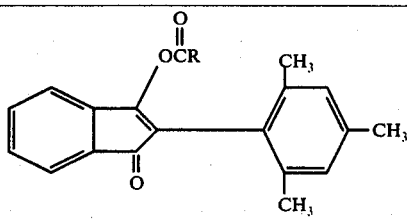

| Name | M. P. °C or IR | Herbicide | Mite Adult | Ova |
|---|---|---|---|---|
| 2-(2',4',6'-Trimethylphenyl)-3-(acetoxy)indone | 115–116 | 39/40 | 5 | 5 |
| 2-(2',4',6'-Trimethylphenyl)-3-(propionyloxy)indone | 109–110.5 | 32/40 | 5 | 5 |
| 2-(2',4',6'-Trimethylphenyl)-3-(isobutyloxy)indone | 78–80 | 37/40 | 5 | 5 |
| 2-(2',4',6'-Trimethylphenyl)-3-(pivaloyloxy)indone | 100–102 | 32/40 | 5 | 5 |
| 2-(2',4',6'-Trimethylphenyl)-3-(2-ethylhexanoyloxy)indone | 66–68 | 29/40 | 5 | 5 |
| 2-(2',4',6'-Trimethylphenyl)-3-(cyclohexanoyloxy)indone | 62–65 | 31/40 | 5 | 5 |
| 2-(2',4',6'-Trimethylphenyl)-3-(neodecanoyloxy)indone (mixture of isomers) | γmax (μ): 5.62 (ester C=O); 5.78 (ketone C=O); 6.1 (enol C=C) | 10/20 | 5 | 5 |
| 2-(2',4',6'-Trimethylphenyl)-3-(Isopropoxycarbonyloxy)indone | 95–96 | 18/20 | 5 | 5 |
| 2-(2',4',6'-Trimethylphenyl)-3-(octadecanoyloxy)indone | 34 | 19/20 | 5 | 5 |
| 2-(2',4',6'-Trimethylphenyl)-3-(methylthioacetoxy)indone | 98–100 | 19/20 | 5 | 5 |
| 2-(2',4',6'-Trimethylphenyl)-3-(3-methoxycarbonylpropionyloxy)indone | γmax (μ): 5.60 (enol ester C=O); 5.78 (ketone and ester (C=O); 6.08 (enol C=C) | 15/15 | 5 | 5 |
| 2-(2',4',6'-Trimethylphenyl)-3-(4-chlorobutyryloxy)indone | 98–100 | 14/15 | 5 | 5 |
| 2-(2',4',6'-Trimethylphenyl)-3-(methoxyacetoxy)indone | 115–117 | 15/15 | 5 | 5 |
| 2-(2',4',6'-Trimethylphenyl)-3-(endo-exo norborn-5-en-2-carbonyloxy)indone | γmax (μ): 5.62 (enol ester C=O); 5.79 (ketone C=O); 6.09 (enol C=C) | 11/15 | 5 | 5 |
| 2-(2',4',6'-Trimethylphenyl)-3-(phenylacetoxy)indone | γmax (μ): 5.59 (enol ester C=O); 5.79 (ketone C=O); 6.09 (enol C=C) | 19/20 | 5 | 5 |
| 2-(2',4',6'-Trimethylphenyl)-3-(dimethylcarbamoyloxy)indone | 117–119 | 14/20 | 3 | 5 |
| 2-(2',4',6'-Trimethylphenyl)-3-(dodecanoyloxy)indone | γmax (μ); 5.59 (enol ester C=O); 5.79 (ketone C=O); 6.09 (enol C=C) | 17/20 | 5 | 5 |
| 2-(2',4',6'-Trimethylphenyl)-3-(undec-9-enoyloxy)indone | γmax (μ): 5.61 (enol ester (C=O); 5.81 (ketone C=O); 6.09 (enol C=C) | 19/20 | 5 | 5 |
| 2-(2',4',6'-Trimethylphenyl)-3-(octyloxycarbonyloxy)indone | γmax (μ): 5.60 (enol ester (C=O); 5.79 (ketone C=O); 6.09 (enol C=C) | 16/20 | 5 | 5 |
| 2-(2',4',6'-Trimethylphenyl)-3-(dodecyloxycarbonyloxy)indone | γmax (μ): 5.61 (enol ester (C=O); 5.80 (ketone C=O); 6.10 (enol C=C) | 17/20 | 5 | 5 |
| 2-(2',4',6'-Trimethylphenyl)-3-(2-ethylhexyloxycarbonyloxy)indone | γmax (μ): 5.61 (enol ester C=O); 5.79 (ketone C=O); 6.09 (enol C=C) | 15/20 | 5 | 5 |
| 2-(2',4',6'-Trimethylphenyl)-3-(octadecyloxycarbonyloxy)indone | 43–45 | 13/15 | 5 | 5 |
| 2-(2',4',6'-Trimethylphenyl)-3-(octylthiocarbonyloxy)indone | γmax (μ): 5.65 Sh (enol ester C=O); 5.78 (ketone C=O); 6.08 (enol C=C) | 11/15 | 5 | 5 |
| 2-(2',4',6'-Trimethylphenyl)-3-(cyclopent-2-en-1-ylacetoxy)indone | γmax (μ): 5.60 (enol ester C=O); 5.80 (ketone (C=O); 6.08 (enol C=C) | 11/15 | 5 | 5 |
| 2-(2',4',6'-Trimethylphenyl)-3-(butyryloxy)indone | 78–80 | 15/15 | 5 | 5 |
| 2-(2',4',6'-Trimethylphenyl)-3-(pentanoyloxy)indone | 67–79 | 15/15 | 5 | 5 |
| 2-(2',4',6'-Trimethylphenyl)-3- | 153–155 | 17/20 | 5 | 5 |

TABLE IV-continued

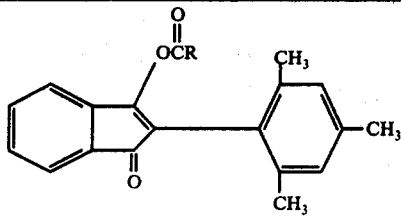

| Name | M. P. °C or IR | Herbicide | Mite Adult | Ova |
|---|---|---|---|---|
| (2-furoyloxy)indone | | | | |
| 2-(2',4',6'-Trimethylphenyl)-3-(2-thenoyloxy)indone | 151–153 | 18/20 | 5 | 5 |
| 2-(2',4',6α-Trimethylphenyl)-3-(3-pyridinecarbonyloxy)-indone | 110–112 | 18/20 | 5 | 5 |
| 2-(2',4',6'-Trimethylphenyl)-3-(chlorocarbonyloxy)indone | 95–97 | 13/20 | 5 | 5 |
| 2-(2',4',6'-Trimethylphenyl)-3-(4-chlorophenyloxycarbonyloxy)indone | 97–98 | 19/20 | 5 | 5 |
| 2-(2',4',6'-Trimethylphenyl)-3-(N-(t-butyl)carbamoyloxy)indone | 145–157 | 15/20 | 5 | 5 |
| 2-(2',4',6'-Trimethylphenyl)-3-(N-butyl-N-methylcarbamoyloxy)indone | γmax (μ): 5.82 (enol ester C=O); 5.88 (ketone C=O); 6.07 (enol C=C) | 4/20 | 1 | 1 |
| 2-(2',4',6'-Trimethylphenyl)-3-(N,N-di(butyl)carbamoyloxy)indone | γmax (μ): 5.84 (enol ester C=O); 5.88 (ketone C=O); 6.19 (enol (C=C) | 10/20 | 3 | 1 |
| 2-(2',4',6'-Trimethylphenyl)-3-(N-methyl-N-phenylcarbamoyloxy)indone | 120–122 | 10/20 | 1 | 3 |
| 2-(2',4',6'-Trimethylphenyl)-3-(4-(morpholino)carbonyloxy)indone | 43–47 | 4/20 | 3 | 5 |
| 2-(2',4',6'-Trimethylphenyl)-3-(piperdinocarbonyloxy)indone | γmax (μ): 5.76 (enol ester C=O); 5.82 (ketone C=O; 6.10 (enol C=C) | 4/20 | 1 | 3 |
| 2-(2',4',6'-Trimethylphenyl)-3-(N-(2,4,6-Trimethylphenyl)-carbamoyloxy)indone | 152–155 | 4/20 | 5 | 5 |
| 2-(2',4',6'-Trimethylphenyl)-3-(N-cyclohexyl-N-methylcarbamoyloxy)-indone | γmax (μ): 5.62 (enol ester C—O); 5.85 (ketone C=O); 6.12 (enol C=C) | 16/20 | 5 | 5 |
| 2(2',4',6'-Trimethylphenyl)-3-(2,4-dichlorophenoxyacetoxy)indone | 113–115 | 20/20 | 5 | 5 |
| 2-(2',4',6'-Trimethylphenyl)-3-(3-(2-(2,4,6-trimethylphenyl)-indon)yloxycarbonyloxy)indone | 221–223 | 15/20 | 5 | 5 |
| 2-(2',4',6'-Trimethylphenyl)-3-(2,4-dimethylallophanoyloxy)indone | γmax (μ): 5.71 (enol ester C=O); 5.8 (ketone C=O); 6.09 (enol C=C) | 16/20 | 1 | 5 |

The data presented in Table V below demonstrates the importance of substitution in the ortho position of the 2-phenyl moiety to achieve biological activity. None of the enol ester compounds described in Table V are substituted in the ortho position. A few are substituted in the para position. All were completely devoid of miticidal or herbicidal activity.

The data presented in Table VI below illustrates the importance of the nature of substituents in the ortho position on the 2-phenyl moiety. All of the enol ester compounds described in Table VI are either monosubstituted in only the ortho position with alkoxy, trifluoromethyl or alkyl (having more than one carbon atom) or are disubstituted only in the ortho positions with alkyl groups (having more than two carbon atoms). None of these compounds exhibits any miticidal or herbicidal activity.

TABLE V

| Name | M. P. °C or IR | Herbicide | Mite Adult | Ova |
|---|---|---|---|---|
| 3-(2-Ethylhexanoyloxy)-2-phenyl-indone | γmax (μ): 5.61 (ester C=O); 5.8 (ketone C=O); 6.12 (enol C=C) | 4/20 | 1 | 1 |
| 2-Phenyl-3-(stearoyloxy)indone | 63–64 | 4/20 | 1 | 1 |
| 2-Phenyl-3-(pivaloyloxy)indone | 102–104 | 8/40 | 1 | 1 |
| 2-Phenyl-3-(acetoxy)indone | 114–116 | 8/40 | 1 | 1 |
| 2-Phenyl-3-(benzoyloxy)indone | 168–169 | 4/20 | 1 | 1 |
| 2-(4'-Chlorophenyl)-3-(pivaloyloxy)indone | 114–116 | 4/20 | 1 | 1 |
| 3-(2-ethylbutanoyloxy)-2-(4'-isopropylphenyl)-indone | γmax (μ): 5.63 (ester C=O); 5.8 (ketone C=O); 6.15 (enol C=C) | 4/20 | 1 | 1 |
| 2-(4'-isopropylphenyl)-3-(pivaloyloxy)indone | 84–87 | 4/20 | 1 | 1 |
| 2-(4'-isopropylphenyl)-3-(palmitoyloxy)indone | γmax (μ): 5.59 (ester C=O); 5.8 (ketone C=O); 6.13 (enol C=C) | 4/20 | 1 | 1 |

TABLE VI

| Name | M. P. ° C or IR | Herbicide | Mite Adult | Ova |
|---|---|---|---|---|
| 2-(2'-Ethylphenyl)-3-pivaloyloxy-indone | γmax (μ): 5.51, 5.68 (ester C=O) 5.81 (ketone C=O); 6.12 enol C=C) | 4/20 | 1 | 1 |
| 2-(2'-isopropylphenyl)-3-pivaloyloxy-indone | γmax (μ): 5.5, 5.63 (ester C=O); 5.80 (ketone C=O); 6.11 (enol C=C) | 4/20 | 1 | 1 |
| 2-(2',6'-diisopropyl)phenyl-3-pivaloyloxy-indone | 168–171 | 3/15 | 1 | 1 |
| 3-(2-Ethylhexanoyloxy)-2-(2'-methoxyphenyl-indone | γmax (μ): 5.5, 5.67 (ester C=O); 5.82 (ketone C=O); 6.1 (enol C=C) | 4/20 | 1 | 1 |
| 2-(2'-Methoxyphenyl)-3-(neodecanoyloxy)-indone | γmax (μ): 5.5, 5.62 (ester C=O) 5.79 (ketone C=O); 6.1 (enol C=C) | 4/20 | 1 | 1 |
| 2-(2'-Methoxyphenyl)-3-(pivaloyloxy)-indone | 90–92 | 8/40 | 1 | 1 |
| 2-(2'-Trifluoromethylphenyl)-3-pivaloyloxy indone | 82–84 | 4/20 | 1 | 1 |

It was also found that a limited class of the enol ester compounds exhibit very powerful fumigant properties. The compounds having this property are those in which the group attached to the carbonyl function of the ester moiety is either alkyl or alkoxy having no more than four carbon atoms.

Two methods were used to evaluate fumigant properties:

Method 1

Fifty mg. of each compound were dissolved in 5 ml. of acetone and poured into a 20 cm. (bottom diameter) Pyrex No. 210 pie plate. The acetone was allowed to evaporate leaving a deposit of approximately 160 μg. per square cm. The plate was then placed in the bottom of a 50 pound metal lard container (about 30 cm. in diameter and 34 cm. high). Two excised bean plants, held in a 250 ml. Erlenmeyer flask containing 100 ml. of tap water and infested with eggs of the two-spotted mite, were placed in the center of the pie plate. The container was held in the insectary (temperature 80°±5° F., 50±5% R. H.) for four days before mortality determinations were made.

Method 2

Excised bean plants infested with egg forms of the two-spotted mite were dipped in an aqueous preparation (500 ppm) of the test compound. The treated plants were transferred to 250 ml. Erlenmeyer flasks containing 100 ml. of tap water. Four flasks holding treated plants were evenly spaced around a similar flask in which were placed untreated mite-infested plants so that the leaves of the treated foliage were in close proximity (1–3 inches) to the untreated plants. Four days later mortality determinations were made.

The results of these experiments are presented in Table VII below. Mortality ratings were as follows:
5 = 80-100% control
3 = moderate control as compared to an unexposed standard
1 = no significant control

TABLE VII

FUMIGANT TOXICITY

| Compound | Fumigant Toxicity Method 1 | Method 2 |
|---|---|---|
| 2-(2',4',6'-Trimethylphenyl)-3-(acetoxy)indone | 5 | 5 |
| 2-(2',4',6'-Trimethylphenyl)-3-(propionyloxy)indone | 5 | 5 |
| 2-(2',4'6'-Trimethylphenyl)-3-(isobutyryloxy)indone | 5 | 5 |
| 2-(2',4',6'-Trimethylphenyl)-3-(pivaloyloxy)indone | 5 | 5 |
| 2-(2',4',6'-Trimethylphenyl)-3-(2-ethylhexanoyloxy)indone | 1 | 1 |
| 2-(2',4',6'-Trimethylphenyl)-3-(cyclohexanoyloxy)indone | 1 | 1 |
| 2-(2',4',6'-Trimethylphenyl)-3-(neodecanoyloxy)indone | 1 | 1 |
| 2-(2',4',6'-Trimethylphenyl)-3-(isopropoxycarbonyloxy)indone | 5 | 3 |
| 2-(2',4',6'-Trimethylphenyl)-3-(octadecanoyloxy)indone | 1 | 1 |
| 2-(2',4',6'-Trimethylphenyl)-3-(3-methoxycarbonylpropionyloxy)indone | 1 | 1 |
| 2-(2',4',6'-Trimethylphenyl)-3-(4-chlorobutyryloxy)indone | 1 | 1 |
| 2-(2',4',6'-Trimethylphenyl)-3-(methoxyacetoxy)indone | 1 | 1 |
| 2-(2',4',6'-Trimethylphenyl)-3-(endo-exo norborn-5-en-2-carbonyloxy)-indone | 1 | 1 |
| 2-(2',4',6'-Trimethylphenyl)-3-(undec-9-enoyloxy)indone | 1 | 1 |
| 2-(2',4',6'-Trimethylphenyl)-3-(dodecyloxycarbonyloxy)indone | 1 | 1 |
| 2-(2',4',6'-Trimethylphenyl)-3-(2-ethylhexyloxycarbonyloxy)indone | 1 | 1 |
| 2-(2',4',6'-Trimethylphenyl)-3-(octylthiocarbonyloxy)indone | 1 | 1 |
| 2(2',4',6'-Trimethylphenyl)-3-(cyclopent-2-en-1-ylacetoxy)indone | 1 | 1 |
| 2-(2',6'-Dichlorophenyl)-3-(pivaloyloxy)indone | — | 3 |

The fumigant properties exhibited by certain of the enol esters is considered highly important due to the fact that these compounds show a high level of activity, even when coverage on an infested plant is discontinuous. These fumigant properties may greatly enhance the uniformity and extent to which control may be achieved in field applications under adverse circumstances.

Side by side comparison tests were conducted to determine the effectiveness of selected enol ester compounds relative to (bis(p-chlorophenyl)trichlorethanol) a miticide sold under the trademark Kelthane and ovex (p-chlorophenyl-p-chlorobenzene sulfonate) two widely used commercial miticides. The tests were conducted in accordance with the procedures described above at various dilutions of the test compounds in order to determine the $LD_{50}$ and $LD_{95}$ values (concentration of test compound required to kill 50 and 95 percent respectively of the mite population.

TABLE VIII

| Compound | Mite Adults (ppm) | | Mita Ova (ppm) | |
|---|---|---|---|---|
|  | $LD_{50}$ | $LD_{95}$ | $LD_{50}$ | $LD_{95}$ |
| 2-(2',4',6'-trimethyl-phenyl)-3-pivaloyloxy indone | 5 | 170 | 3 | 9 |
| 2-(2',4',6'-trimethyl-phenyl)-3-(2-ethyl-hexanoyloxy)indone | 25 | 230 | 2 | 6 |
| Kelthane | 20 | 65 | 370 | 700 |
| Ovex | 1000 | — | 200 | 300 |

Both of the enol ester compounds tested are dramatically superior to Kelthane and ovex for control of mite ova and also show good control of mite adults.

Experiments were also conducted to determine the phytotoxicity of representative enol ester compositions with respect to healthy fresh plants. Solutions of the desired compound were prepared as described above to provide a concentration of 2500 parts per million of the enol ester compound. The test plants were sprayed in accordance with the procedure described above for the Mite Foliage Spray Test so as to deliver approximately 100 milliliters of test solution to the leaves of each plant tested. The sprayed plants and controls were set aside for approximately 1 hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

TABLE IX

| Compound | Phytotoxicity Rating | | | |
|---|---|---|---|---|
|  | Bean | Corn | Tomato | Cotton |
| 3-(2-Ethylhexanoyloxy)-2-(2'-fluorophenyl)indone | 2 | 2 | 1 | 1 |
| 2-(2'-Chlorophenyl)-3-(pivaloyloxy)indone | 1 | 1 | 1 | 1 |
| 2-(2'-Chlorophenyl)-3-(2-methylpentanoyloxy)indone | 1 | 1 | 1 | 1 |
| 2-(2'-Bromophenyl)-3-(pivaloyloxy)indone | 1 | 1 | 1 | 1 |
| 2-(2'-Chlorophenyl)-3-(stearoyloxy)indone | 1 | 1 | 1 | 1 |
| 2-(2'-Chloro-6'-methylphenyl)-3-(pivaloyloxy)indone | 1 | 1 | 3 | 2 |
| 2-(2'-Methylphenyl)-3-(pivaloyloxy)indone | 1 | 1 | 1 | 1 |
| 3-(2-Ethylhexanoyloxy)-2-(2'-methylphenyl)indone | 1 | 1 | 1 | 1 |
| 2-(2'Methylphenyl)-3-(palmitoyloxy)indone | 1 | 1 | 1 | 1 |
| 2-(2'-Methylphenyl)-3-(neodecanoyloxy)indone | 1 | 1 | 1 | 1 |
| 2-(2',4'-Dimethylphenyl)-3-(stearoyloxy)indone | 1 | 1 | 1 | 1 |
| 2(2',4'-Dimethylphenyl)-3-(lauroyloxy)indone | 1 | 1 | 1 | 1 |
| 2(2',4'-Dimethylphenyl)-3-(2-methylpentanoyloxy)indone | 1 | 1 | 1 | 1 |
| 2-(2',6'-Dimethylphenyl)-3-(pivaloyloxy)indone | 1 | 1 | 3 | 2 |
| 2-(2',5'-Dimethylphenyl)-3-(neodecanoyloxy)indone (mixture of isomers) | 1 | 1 | 1 | 1 |
| 2-(2',5'-Dimethylphenyl)-3-(2-ethylbutanoyloxy)indone | 1 | 1 | 1 | 1 |
| 2-(2',5'-Dimethylphenyl)-3-(tridecanoyloxy)indone | 2 | 2 | 1 | 1 |
| 2-(2',6'-Dimethyl-4-t-butylphenyl)-3-(pivaloyloxy)indone | 1 | 1 | 1 | 1 |
| 2-(2',6'-Dimethyl-4-methoxyphenyl)-3-(pivaloyloxy)indone | 1 | 1 | 1 | 1 |
| 3-(Pivaloyloxy)-2-(6'-methoxy-2',3',4'-trimethylphenyl)indone | 1 | 1 | 1 | 1 |
| 3-(2-Ethylhexanoyloxy)-2-(1-naphthyl)indone | 1 | 1 | 1 | 1 |
| 2-(2',4',6'-Trimethylphenyl)-3-(acetoxy)indone | 1 | 1 | 2 | 2 |
| 2-(2',4',6'-Trimethylphenyl)-3-(propionyloxy)indone | 1 | 2 | 2 | 1 |
| 2-(2',4',6'-Trimethylphenyl)-3-(isobutyryloxy)indone | 1 | 4 | 2 | 2 |
| 2-(2',4',6'-Trimethylphenyl)-3-(pivaloyloxy)indone | 1 | 3 | 3 | 3 |
| 2-(2',4',6'-Trimethylphenyl)-3-(2-ethylhexanoyloxy)indone | 2 | 1 | 1 | 1 |
| 2-(2',4',6'-Trimethylphenyl)-3-(cyclohexanoyloxy)indone | 1 | 1 | 2 | 2 |
| 2-(2',4',6'-Trimethylphenyl)-3-(neodecanoyloxy)indone (mixture of isomers) | 2 | 2 | 1 | 1 |
| 2-(2',4',6'-Trimethylphenyl)-3-(isopropoxycarbonyloxy)indone | 2 | 1 | 1 | 1 |
| 2-(2',4',6'-Trimethylphenyl)-3-(octadecanoyloxy)indone | 1 | 1 | 1 | 1 |
| 2-(2',4',6'-Trimethylphenyl)-3-(3-methoxycarbonyl propionyloxy)-indone | 1 | 1 | 1 | 1 |
| 2-(2',4',6'-Trimethylphenyl)-3-(endo-exo norborn-5-en-2-carbonyloxy)indone | 1 | 1 | 1 | 2 |
| 2-(2',4',6'-Trimethylphenyl)-3-(undec-9-enoyloxy)indone | 2 | 2 | 2 | 1 |
| 2-(2',4',6'-Trimethylphenyl)-3-(dodecyloxycarbonyloxy)indone | 1 | 2 | 1 | 1 |
| 2-(2',4',6'-Trimethylphenyl)-3-(2-ethylhexyloxycarbonyloxy)-indone | 1 | 2 | 1 | 1 |
| 2-(2',4',6'-Trimethylphenyl)-3-(octylthiocarbonyloxy)indone | 1 | 1 | 1 | 1 |
| 2-(2',4',6'-Trimethylphenyl)-3-(cyclopert-2-en-1-ylacetoxy)indone | 1 | 1 | 1 | 2 |
| 2-(2',4',6'-Trimethylphenyl)-3-(4-chlorobutyryloxy)indone | 1 | 2 | 2 | 2 |
| 2-(2',4',6'-Trimethylphenyl)-3-(methoxyacetoxy)indone | 1 | 1 | 1 | 1 |

The test results presented in Table IX above, indicate that these materials may be used on certain economic crops without danger of phytotoxicity even at application rates considerably higher than would normally be used in field applications.

In Table X below test results obtained in small scale field testing are presented to demonstrate the significantly higher degree of mite control achieved with the enol esters as opposed to the parent indandione compound from which the enol ester is prepared.

Selected enol ester compositions were evaluated in small scale field tests to determine whether the excellent miticidal properties observed in greenhouse testing would be obtained under actual conditions of field use. Comparison tests were made with the parent indandione compositions of the enol esters selected for field evaluation to establish whether the superior results observed in laboratory evaluations would carry over into actual conditions of use in the field. Although normally, field tests conditions are difficult to control precisely, the results obtained from these tests demonstrate conclusively that the enol esters of this invention are consistently and significantly superior to the parent indandione compounds in miticidal activity under actual conditions of use in the field and that the outstanding miticidal properties observed in laboratory testing are maintained under field conditions.

In Test I 500 ppm aqueous dispersions were prepared as described above. In tests II and III various dilutions of the test compounds ranging from 125 ppm to 1000 ppm were prepared and used. In each case the test dispersions were applied to a minimum of two replicate test plots measuring five feet in length and containing healthy young Tendergreen bean plants which had previously been infested with two spotted mite (*Tetranychus urticae* (Koch)). Dispersions of the test compounds at each concentration level were applied to individual replicate plots using one-half gallon garden sprayers equipped with spray nozzles to apply approximately 250 ml of test solution to each replicate. The effectiveness of the treatment was determined at intervals following application, by microscopic examination of five leaves selected at random from each replicate plot. The degree of effectiveness for each leaf was rated on a scale of from 1 to 5 with 1 indicating no control in reference to a standard sprayed with a mixture of solution less test compound and 5 indicating complete control. The results obtained from inspection of sample leaves were then averaged to give a numerical indication of the degree of control for each compound tested at the concentration applied.

The following compounds were evaluated in these experiments:

Compound A: 2-(2',4',6'-trimethylphenyl)-1,3-indandione
Compound A1: 2-(2',4',6'-trimethylphenyl)-3-(pivaloyloxy)indone
Compound A2: 3-(3-chlorobenzoyloxy)-2-(2',4',6'-trimethylphenyl)indone
Compound A3: 3-(2-chlorobenzoyloxy)-2-(2',4',6'-trimethylphenyl)indone
Compound B: 2-(2',6'-dichlorophenyl)-1,3-indandione
Compound B1: 2-(2',6'-dichlorophenyl)-3-(pivaloyloxy)indone
Compound B2: 3-(3-chlorobenzoyloxy)-2-(2',6'-dichlorophenyl)indone
Compound B3: 3-(2-chlorobenzoyloxy)-2-(2',6'-dichlorophenyl)indone The results of these tests are recorded in Table X below:

control frequently observed for the enol ester compounds in the second and third readings is indicative of the high residual activity and excellent ovicidal activity possessed by these compounds particularly when compared to the parent indandione compounds (Compounds A and B).

The new compounds of this invention may be applied as miticides and herbicides according to methods known to those skilled in the art. Pesticidal compositions containing the compounds as the active toxicant will usually comprise a carrier and/or a diluent, either liquid or solid.

Suitable liquid diluents or carriers include water, petroleum distillates, or other liquid carriers with or without surface active agents. Liquid concentrates may be prepared by dissolving one of these compounds with a non-phytotoxic solvent such as acetone, xylene, or nitrobenzene and dispersing the toxicants in water with the aid of suitable surface active smulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, such as the condensation products of alkylene oxides with phenol and organic acids, alkyl, aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight Satisfactory sprays, dusts, or granules for general use contain from about ¼ to 15 pounds of active toxicant per acre.

TABLE X

| AVERAGE MITE CONTROL RATINGS SMALL SCALE FIELD TESTS | | | | | | | | | | | | | | | | | |
|---|---|---|---|---|---|---|---|---|---|---|---|---|---|---|---|---|---|
| Conc. (ppm) | 1st. Reading* | | | | | | | | 2nd Reading | | | | | | | 3rd Reading | |
| | A | A1 | A2 | A3 | B | B1 | B2 | B3 | A | A1 | A2 | A3 | B | B1 | B2 | B3 | A | A1 |
| TEST I | | | | | | | | | | | | | | | | | | |
| 500 | 1.0 | 4.0 | 1.5 | 2.5 | 1.5 | 3.5 | 3.0 | 3.0 | 1.0 | 3.5 | 2.0 | 2.0 | 2.0 | 4.0 | 3.0 | 2.5 | — | — |
| TEST II | | | | | | | | | | | | | | | | | | |
| 250 | 1.0 | 3.0 | — | — | 3.7 | 2.3 | — | — | 1.3 | 4.0 | — | — | 2.3 | 3.7 | — | — | — | — |
| 500 | 2.7 | 2.3 | — | — | 3.0 | 3.0 | — | — | 1.7 | 4.7 | — | — | 3.3 | 3.3 | — | — | — | — |
| 1000 | — | — | — | — | 2.0 | 3.3 | — | — | — | — | — | — | 3.3 | 4.7 | — | — | — | — |
| TEST III | | | | | | | | | | | | | | | | | | |
| 125 | — | 1.7 | — | — | — | — | — | — | — | 2.3 | — | — | — | — | — | — | — | 1.7 |
| 250 | 1.0 | 3.0 | — | — | — | — | — | — | 2.0 | 4.0 | — | — | — | — | — | — | — | 3.7 |
| 500 | 1.3 | 3.0 | — | — | — | — | — | — | 1.7 | 4.0 | — | — | — | — | — | — | — | 4.5 |
| 1000 | 3.3 | — | — | — | — | — | — | — | 3.3 | — | — | — | — | — | — | — | 2.3 | — |

*1st Reading: Test I, 4 days after application, Tests II & III 3 days after application
2nd Reading: Test I, 8 days after application, Tests II & III 7 days after application
3rd Reading: 21 days after application.
Dashes indicate no test conducted.

The test results from the small scale field tests demonstrate the very high degree of miticidal activity possessed by the enol ester compounds (Compounds A1–A3 and B1–B3). The improvement in the degree of The pesticides contemplated herein prevent attack by mites upon plants or other material to which the pesticides are applied, and they have high residual toxicity. The toxicants are chemically inert and they are compatible with substantially any other constituents of the spray schedule. When used as miticides they will normally be applied to the foliage of the plants to be treated. When used as herbicides they may be used in the soil or directly upon the seeds to be treated.

What is claimed is:

1. A pre-emergent herbicide comprising an extender and as an active toxicant a herbicidally effective amount of a compound having the structural formula:

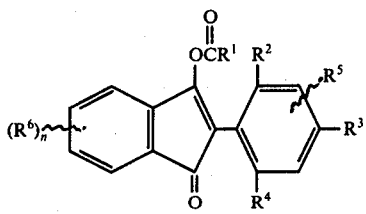

wherein:
  $R^1$ is hydrogen, halogen or an organic radical;
  $R^2$ is hydrogen, methyl, ethyl, methoxy, ethoxy, fluorine, chlorine, bromine, trichloromethyl, trifluoromethyl or mixed chlorofluoromethyl;
  $R^3$ is hydrogen, lower alkyl, lower alkoxy, fluorine, chlorine, bromine, nitro, acylamido, trichloromethyl, trifluoromethyl or mixed chlorofluoromethyl;
  $R^4$ is methyl, ethyl, methoxy, ethoxy, fluorine, chlorine or bromine;
  $R^5$ is hydrogen, lower alkyl, lower haloalkyl, lower alkoxy, acylamido, fluorine, chlorine or bromine;
  $R^6$ is hydrogen, lower alkyl, lower alkoxy, fluorine, chlorine, bromine, trifluoromethyl, trichloromethyl or acylamido;
  $n$ is a small whole number from 1 to 4; and
  $R^2$ and $R^5$ or $R^4$ and $R^5$ taken together, may be —CH=CH—CH=CH— with the proviso that when $R^4$ is ethyl, methoxy or ethoxy $R^2$, $R^3$ and $R^5$ may not all be hydrogen.

2. A pre-emergent herbicide in accordance with claim 1 wherein $R^1$ is hydrogen chloro, bromo, fluoro or an unsubstituted or substituted organic radical selected from the group consisting of: alkyl, alkenyl, alkynyl, cycloalkyl, cycloalkenyl, alkylthioalkyl, alkoxyalkyl, alkoxycarbonylalkyl, arylalkyl, aryloxyalkyl, arylthioalkyl, aryl, alkylaryl, alkoxyaryl, alkoxy, alkylthio, aryloxy, arylthio, heterocyclic acylamido alkyl carbamoylalkyl and amino radicals having the formula:

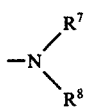

wherein $R^7$ is hydrogen, alkyl, alkenyl, alkynyl, cycloalkyl or aryl and $R^8$ is alkyl, alkenyl, alkynyl, cycloalkyl or aryl or $R^7$ and $R^8$, taken together, form a lower alkylene or lower dialkylene ether linkage.

3. A pre-emergent herbicide, adult miticide and mite ovicide comprising an extender and as an active toxicant an herbicidally, miticidally or mite ovicidally effective amount of a compound having the structural formula:

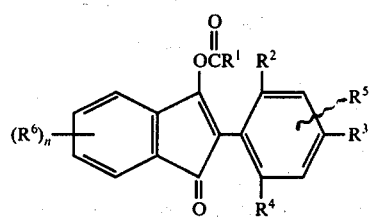

wherein:
  $R^1$ is chlorine, bromine, fluorine or an organic radical, which does not interfere with hydrolysis of the ester moiety to which it is attached;
  $R^2$ is hydrogen, methyl, ethyl, methoxy, fluorine, chlorine or bromine;
  $R^3$ is hydrogen, lower alkyl, lower alkoxy, fluorine, chlorine or bromine;
  $R^4$ is methyl, ethyl, methoxy, fluorine, chlorine or bromine;
  $R^5$ is hydrogen, lower alkyl, lower alkoxy, fluorine, chlorine or bromine;
  $R^6$ is hydrogen, lower alkyl, lower alkoxy, fluorine chlorine or bromine; and
  $n$ is a small whole number from 1 to 4 with the proviso that when $R^4$ is ethyl or methoxy, $R^2$, $R^3$ and $R^5$ may not all be hydrogen.

4. A herbicide, miticide and ovicide in accordance with claim 3 wherein $R^1$ is fluorine, chlorine, bromine or an unsubstituted or substituted organic radical selected from the group consisting of: alkyl, alkenyl, alkynyl, cycloalkyl, cycloalkenyl, alkylthioalkyl, alkoxyalkyl, alkoxycarbonylalkyl, arylalkyl, aryloxyalkyl, arylthioalkyl, aryl, alkylaryl, alkoxyalkyl, alkoxy, alkylthio, aryloxy, arylthio, aryloxy, arylthio, heterocyclic, acylamidoalkyl carbamoylalkyl and amino radicals having the formula:

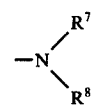

wherein $R^7$ is hydrogen, alkyl, alkenyl, alkynyl, cycloalkyl or aryl and $R^8$ is alkyl, alkenyl, alkynyl, cycloalkyl or aryl or $R^7$ and $R^8$, taken together, form a lower dialkylene ether linkage.

5. A herbicide, miticide and ovicide in accordance with claim 3 wherein $R^1$ is aryl having at least one unsubstituted carbon in the ortho position.

6. A herbicide, miticide and ovicide in accordance with claim 3 wherein $R^2$ is hydrogen, methyl, chlorine or bromine and $R^4$ is methyl, chlorine or bromine.

7. A pre-emergent herbicide, adult miticide and mite ovicide comprising an extender and as an active toxicant an herbicidally, miticidally or mite ovicidally effective amount of a compound having the structural formula:

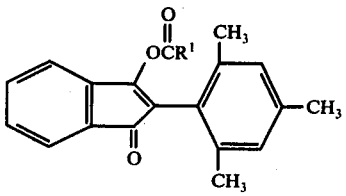

wherein R¹ is chlorine, bromine, fluorine or an organic radical which does not interfere with hydrolysis of the ester moiety to which it is attached.

8. A herbicide, miticide and ovicide in accordance with claim 7 wherein R¹ is phenyl.

9. A herbicide, miticide and ovicide in accordance with claim 7 wherein R¹ is heptadecyl.

10. A herbicide, miticide and ovicide in accordance with claim 7 wherein R¹ is isopropoxy.

11. A herbicide, miticide and ovicide in accordance with claim 7 wherein R¹ is octadecyloxy.

12. A pre-emergent herbicide, adult miticide and mite ovicide comprising an extender and as an active toxicant an herbicidally, miticidally or mite ovicidally effective amount of a compound having the structural formula:

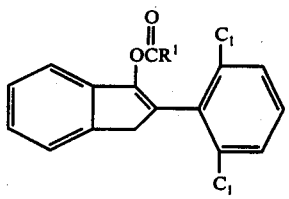

wherein R¹ is chlorine, bromine, fluorine or an organic radical which does not interfere with the hydrolysis of the ester moiety to which it is attached.

13. A pre-emergent herbicide, adult miticide and mite ovicide comprising an extender and as an active toxicant an herbicidally, miticidally, or mite ovicidally effective amount of a compound having the structural formula:

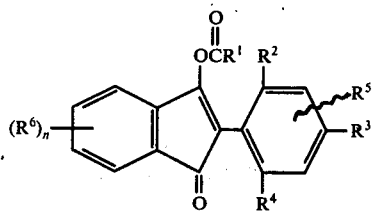

wherein:
R¹ is alkyl;
R² is hydrogen, methyl, ethyl, methoxy, fluorine, chlorine or bromine;
R³ is hydrogen, lower alkyl, lower alkoxy, fluorine, chlorine or bromine;
R⁴ is methyl, ethyl, methoxy, fluorine, chlorine or bromine;
R⁵ is hydrogen, lower alkyl, lower alkoxy, fluorine, chlorine or bromine;
R⁶ is hydrogen, lower alkyl, lower alkoxy, fluorine, chlorine or bromine; and n is a small whole number from 1 to 4 with the proviso that when R⁴ is ethyl or methoxy, R², R³ and R⁵ may not all be hydrogen.

14. A herbicide, miticide and ovicide in accordance with claim 13 wherein R¹ is alkyl having from 1 to 4 carbon atoms.

15. A pre-emergent herbicide, adult miticide and mite ovicide comprising an extender and as an active toxicant an herbicidally, miticidally, or mite ovicidally effective amount of a compound having the structural formula:

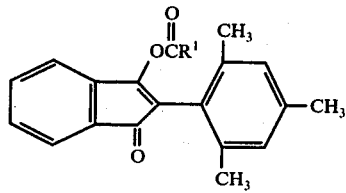

wherein R¹ is alkyl;

16. A herbicide, miticide and ovicide in accordance with claim 15 wherein R¹ is alkyl having from 1 to 4 carbon atoms.

17. A herbicide, miticide and ovicide in accordance with claim 15 wherein R¹ is methyl.

18. A herbicide, miticide and ovicide in accordance with claim 15 wherein R¹ is ethyl.

19. A herbicide, miticide and ovicide in accordance with claim 15 wherein R¹ is isopropyl.

20. A herbicide, miticide and ovicide in accordance with claim 15 wherein R¹ is t-butyl.

21. A herbicide, miticide and ovicide in accordance with claim 15 wherein R¹ is 1-ethylpentyl.

22. A pre-emergent herbicide, adult miticide and mite ovicide comprising an extender and as an active toxicant as herbicidally, miticidally, or mite ovicidally effective amount of a compound having the structural formula:

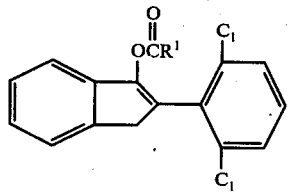

wherein R¹ is alkyl.

23. A method of controlling plant pests which comprises applying to the seeds of such plant pests a herbicidally effective amount of a compound described in claim 1.

24. A method of controlling mites which comprises subjecting them to a miticidal amount of a compound described in claim 3.

25. A method of controlling mites which comprises subjecting them to a miticidal amount of a compound described in claim 4.

26. A method of controlling mites which comprises subjecting them to a miticidal amount of a compound described in claim 6.

27. A method of controlling mites which comprises subjecting them to a miticidal amount of a compound described in claim 7.

28. A method of controlling mites which comprises subjecting them to a miticidal amount of a compound described in claim 12.

29. A method of controlling mites which comprises subjecting them to a miticidal amount of a compound of the formula:

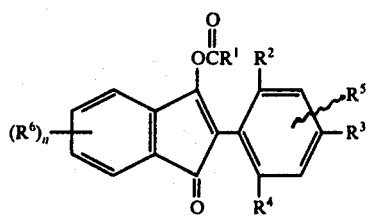

wherein:

$R^1$ is alkyl;

$R^2$ is hydrogen, methyl, ethyl, methoxy, fluorine, chlorine or bromine;

$R^3$ is hydrogen, lower alkyl, lower alkoxy, fluorine, chlorine or bromine;

$R^4$ is methyl, ethyl, methoxy, fluorine, chlorine or bromine;

$R^5$ is hydrogen, lower alkyl, lower alkoxy, fluorine, chlorine or bromine;

$R^6$ is hydrogen, lower alkyl, lower alkoxy, fluorine, chlorine or bromine; and $n$ is a small whole number from 1 to 4 with the proviso that when $R^4$ is ethyl or methoxy, $R^2$, $R^3$ and $R^5$ may not all be hydrogen.

30. A method according to claim 29 wherein $R^1$ is lower alkyl having from 1 to 4 carbon atoms.

31. A method according to claim 29 wherein $R^2$, $R^3$ and $R^4$ are methyl and $R^5$ and $R^6$ are hydrogen.

32. A method according to claim 29 wherein $R^2$ and $R^4$ are chlorine and $R^3$, $R^5$ and $R^6$ are hydrogen.

33. A method according to claim 29 wherein $R^1$ is lower alkyl having from 1 to 4 carbon atoms; $R^2$ and $R^4$ are chlorine and $R^3$, $R^5$ and $R^6$ are hydrogen.

34. A herbicide, miticide and ovicide in accordance with claim 22 wherein $R^1$ is alkyl having from 1 to 4 carbon atoms.

* * * * *

UNITED STATES PATENT OFFICE
CERTIFICATE OF CORRECTION

Patent No. 4,104,043              Dated  August 1, 1978

Inventor(s) John A. Durden, Jr., Anthony A. Sousa, John F. Stephen

It is certified that error appears in the above-identified patent and that said Letters Patent are hereby corrected as shown below:

Column 17, Table III, lines 43 - 45 which read
"
2-2',5'-Dimethylphenyl)-3-(2-ethylbutanoyloxy)-indone $\lambda$max ($\mu$):              4/20     3     5"
    5.65 (ester C=O);
    5.8 (deonte C=O);  6.1(enol C=C)

should read --

2-(2',5'-Dimethylphenyl)-3-(2-ethylbutanoyloxy)indone $\lambda$max ($\mu$):              4/20     3     5 --
    5.65 (ester C=O);
    5.8 (ketone C=O);
    6.1 (enol C=C)

UNITED STATES PATENT OFFICE
CERTIFICATE OF CORRECTION

Patent No. 4,104,043    Dated August 1, 1978

Inventor(s) John A. Durden, Jr., Anthony A. Sousa, John F. Stephen

It is certified that error appears in the above-identified patent and that said Letters Patent are hereby corrected as shown below:

Column 21, line 5 which reads "2-(2',4', 6a-Trimethylphenyl)-3-" should read

-- 2-(2',4',6'-Trimethylphenyl)-3- --.

Column 28, line 19, which reads "smulsifying" should read -- emulsifying --.

Column 30, line 40, which reads "alkoxyalkyl," should read -- alkoxyaryl, --.

Column 32, line 39, which reads "as" should read -- an --.

UNITED STATES PATENT OFFICE
CERTIFICATE OF CORRECTION

Patent No. 4,104,043　　　　Dated August 1, 1978

Inventor(s) John A. Durden, Jr., Anthony A. Sousa, John F. Stephen

It is certified that error appears in the above-identified patent and that said Letters Patent are hereby corrected as shown below:

Column 31, lines 28 through 37, the formula which reads

"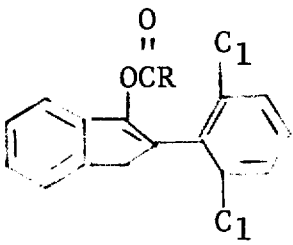"

should read,

-- 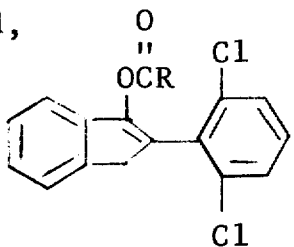 --

UNITED STATES PATENT OFFICE
CERTIFICATE OF CORRECTION

Patent No. 4,104,043　　　　　　　Dated August 1, 1978

Inventor(s) John A. Durden, Jr., Anthony A. Sousa, John F. Stephen

It is certified that error appears in the above-identified patent and that said Letters Patent are hereby corrected as shown below:

Column 32, lines 41 through 50, the formula which reads,

"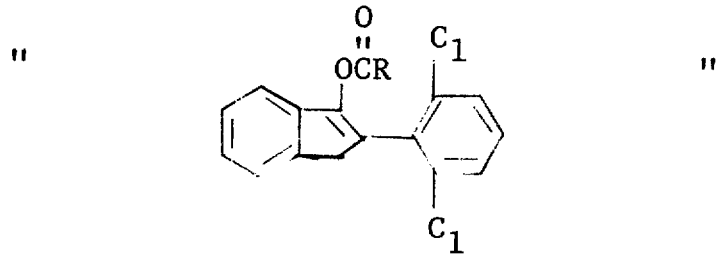"

should read

--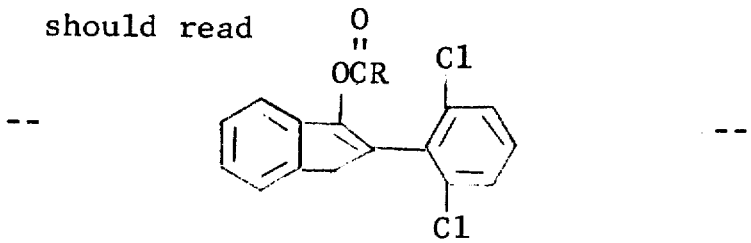--

Signed and Sealed this
Thirteenth Day of February 1979

[SEAL]

Attest:

RUTH C. MASON
Attesting Officer

DONALD W. BANNER
Commissioner of Patents and Trademarks